United States Patent [19]
Cohn et al.

[11] Patent Number: 5,941,892
[45] Date of Patent: *Aug. 24, 1999

[54] SURGICAL SCALPEL

[75] Inventors: Simon Cohn, North Arlington, N.J.; Arthur C. Sonderland, Pawleys Island, S.C.; Michael J. Carter, Monmouth Junction, N.J.; Noel Gharibian, Glendale, Calif.

[73] Assignee: Becton, Dickinson and Company, Franklin Lakes, N.J.

[*] Notice: This patent is subject to a terminal disclaimer.

[21] Appl. No.: 09/052,230

[22] Filed: Mar. 31, 1998

Related U.S. Application Data

[63] Continuation-in-part of application No. 08/666,734, Jun. 18, 1996, which is a continuation-in-part of application No. 08/376,065, Jan. 20, 1995, Pat. No. 5,527,329, which is a continuation of application No. 08/163,938, Dec. 8, 1993, abandoned.

[51] Int. Cl.⁶ .................................................. A61B 17/32
[52] U.S. Cl. .................................. 606/167; 30/2; 30/151; 30/335
[58] Field of Search .................................. 606/166, 167, 606/170; 30/2, 151, 158, 167, 335, 339

[56] References Cited

U.S. PATENT DOCUMENTS 5,662,669  9/1997  Abidin et al. ........................... 606/167

*Primary Examiner*—Michael Buiz
*Assistant Examiner*—William W. Lewis
*Attorney, Agent, or Firm*—Arthur D. Dawson

[57] ABSTRACT

A surgical scalpel includes an elongate handle that has a proximal end, a open distal end and sidewalls that define an upwardly open cavity with a bottom with an open void therein. The sidewalls each have an elongate channel therein. The scalpel of the invention includes a cartridge that is removably retained within the cavity. The cartridge includes a shield. The cartridge has a blade holder with a proximal end and a distal end mounted within the shield for slidable movement between a proximal and a distal position. There is a latch on the blade holder for engaging the handle and the shield to retain releasably the blade holder in the distal position and the proximal position. The scalpel has a blade fixedly attached to the blade holder so that when the blade holder is in the distal position, the blade projects distally from the handle. When the blade holder is in the proximal position, the blade is within the shield and the handle and thus substantially protected from inadvertent exposure.

21 Claims, 38 Drawing Sheets

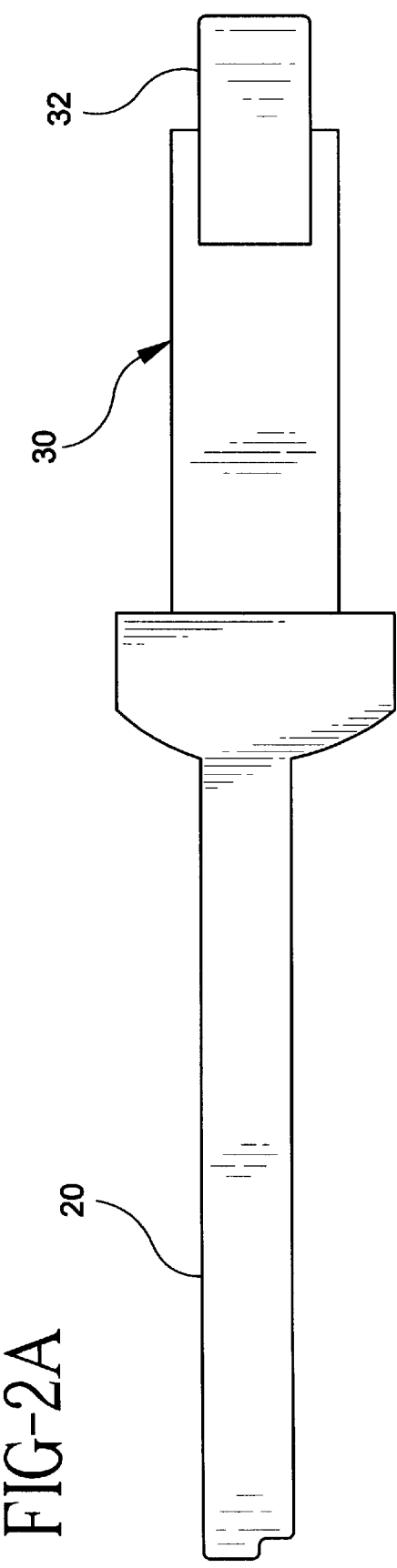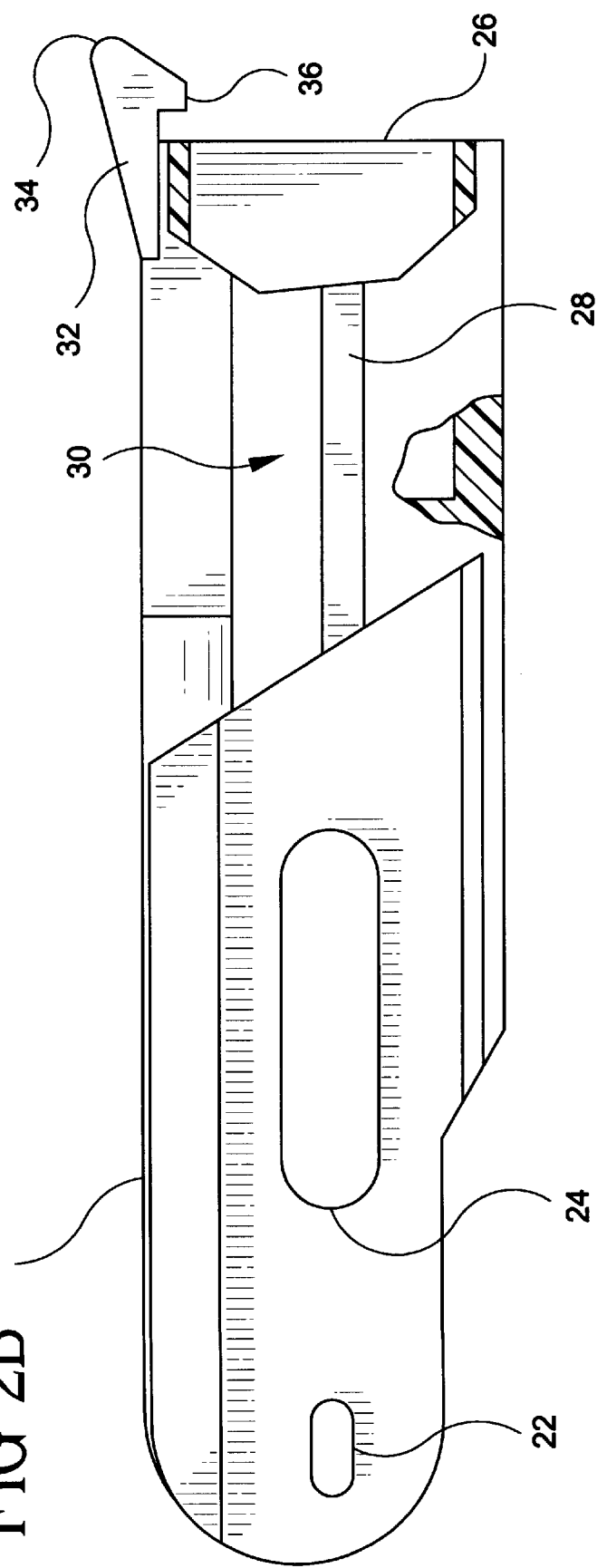

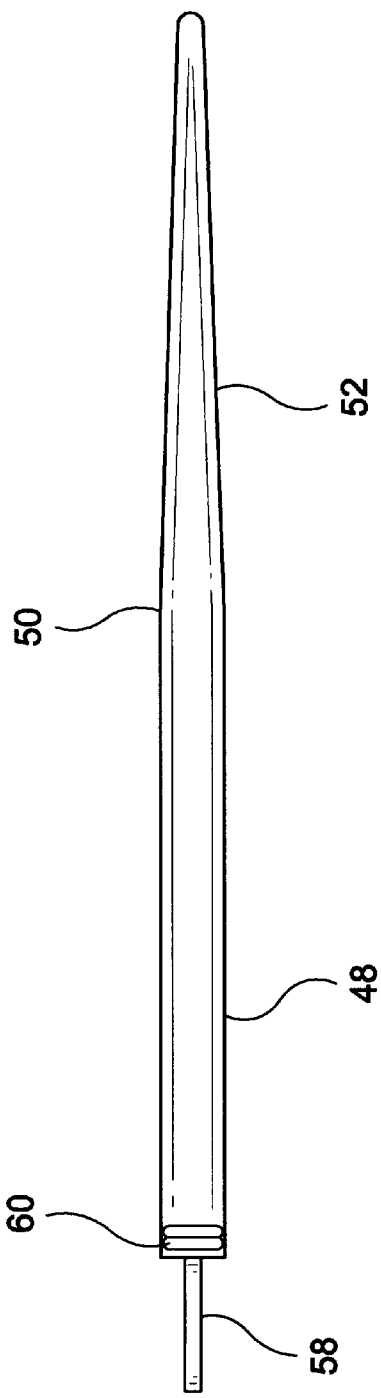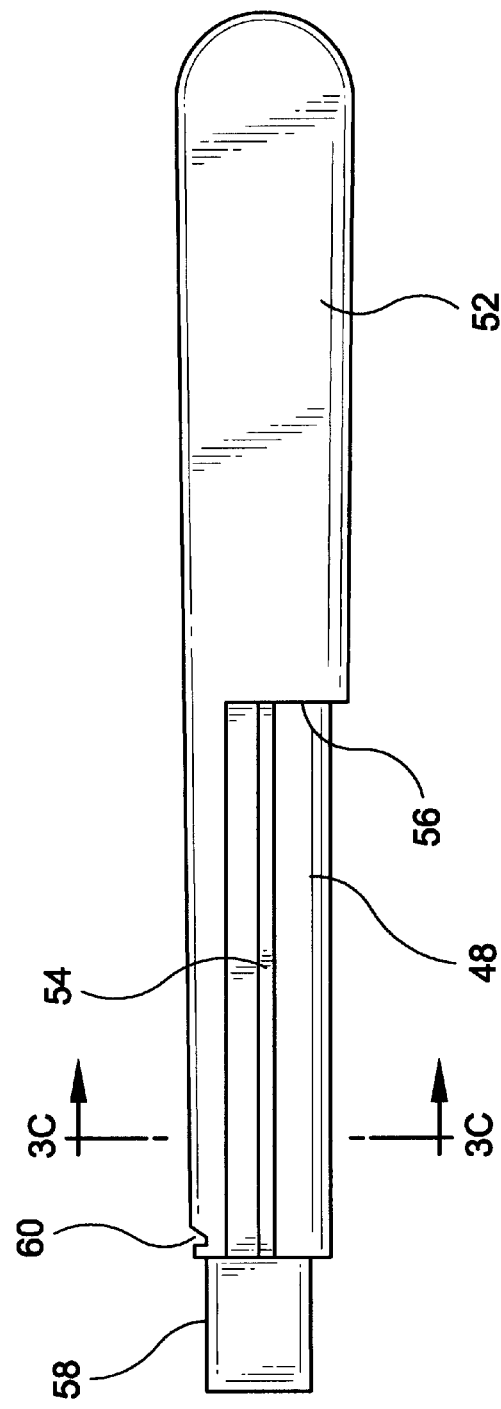

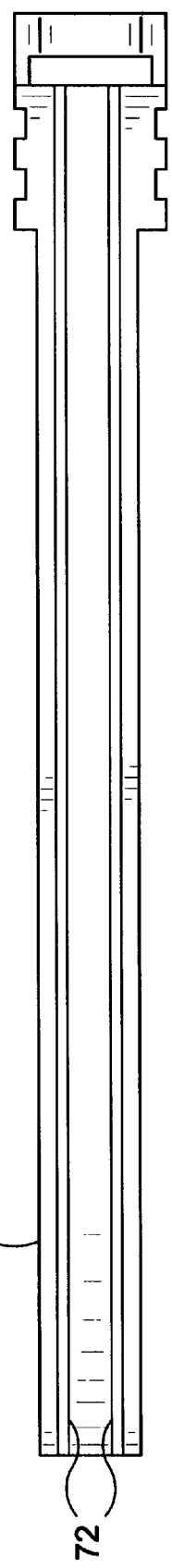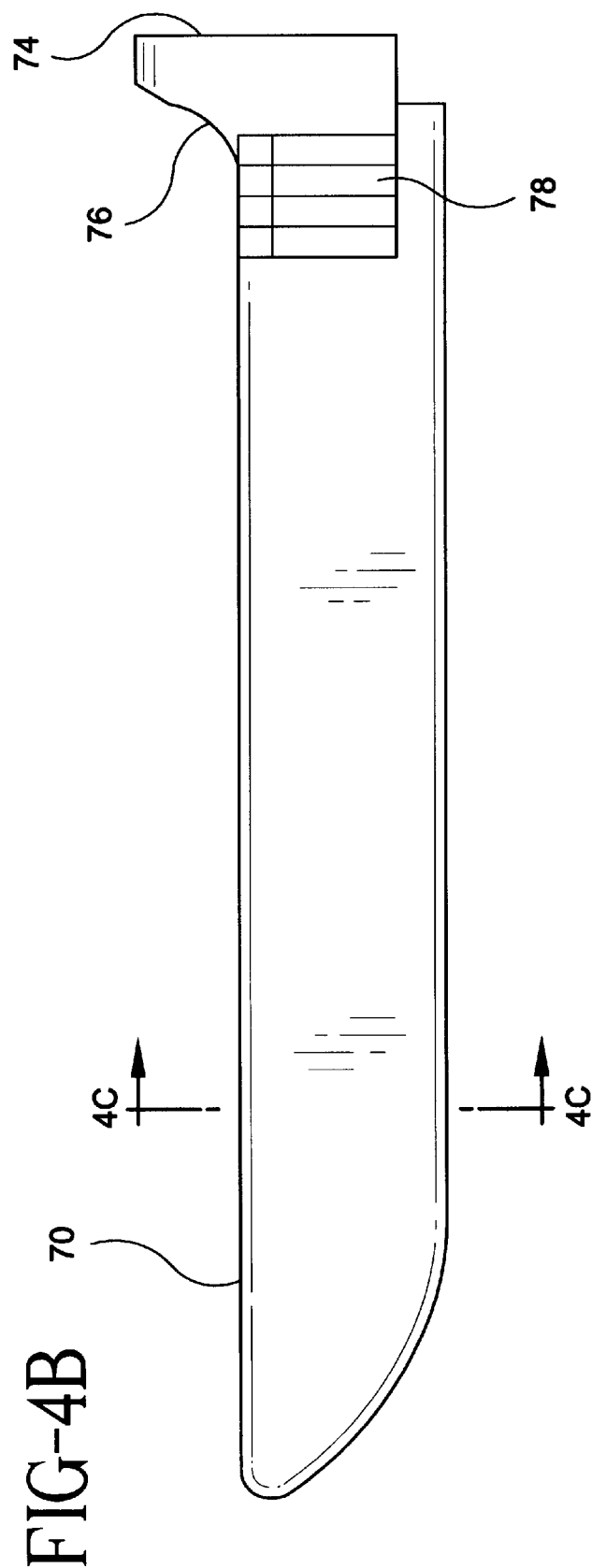
FIG-4A
FIG-4B

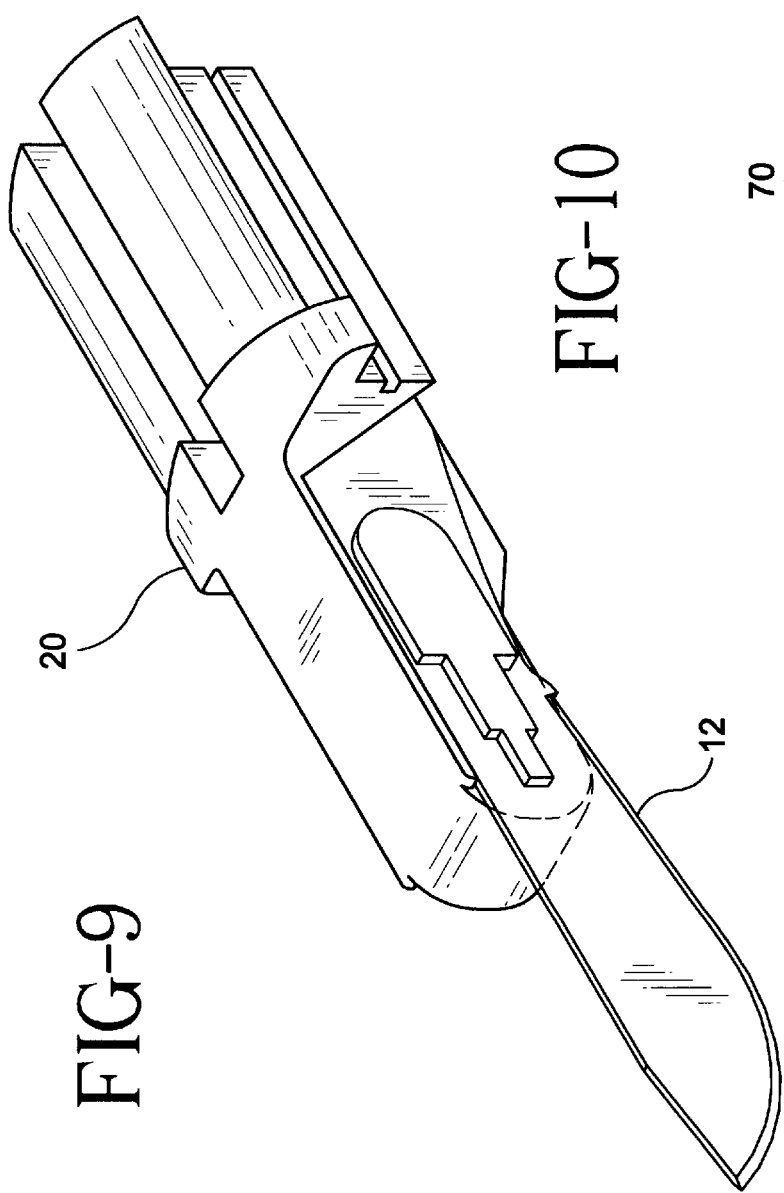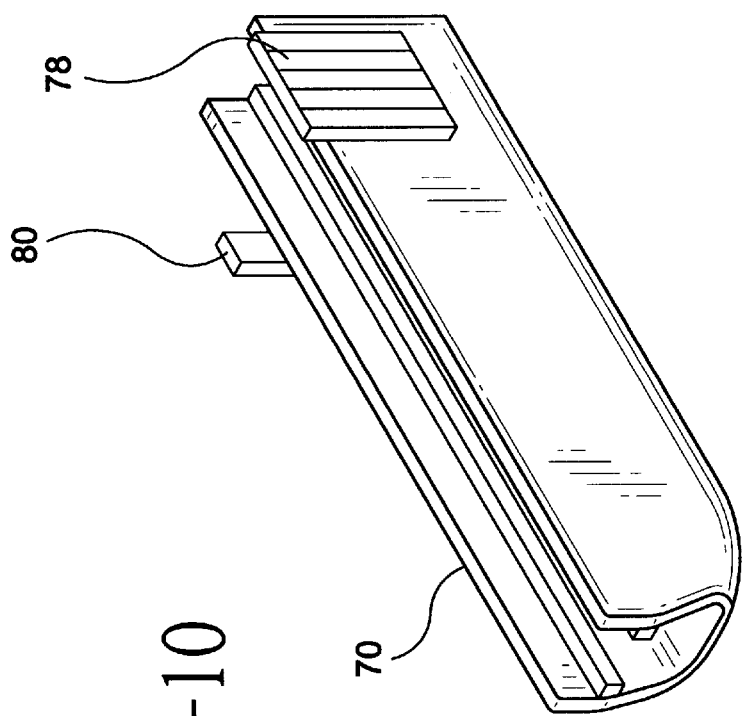

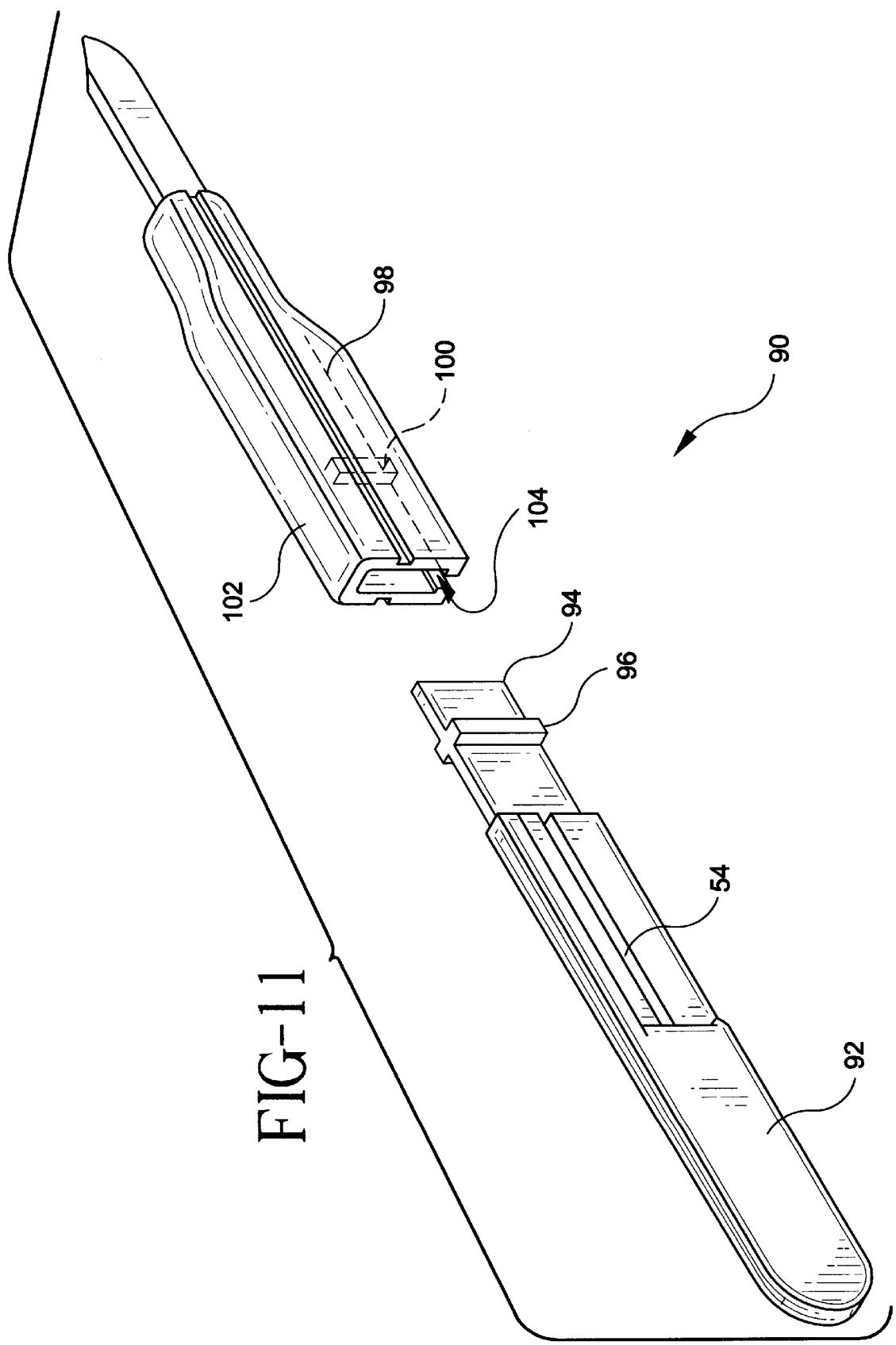

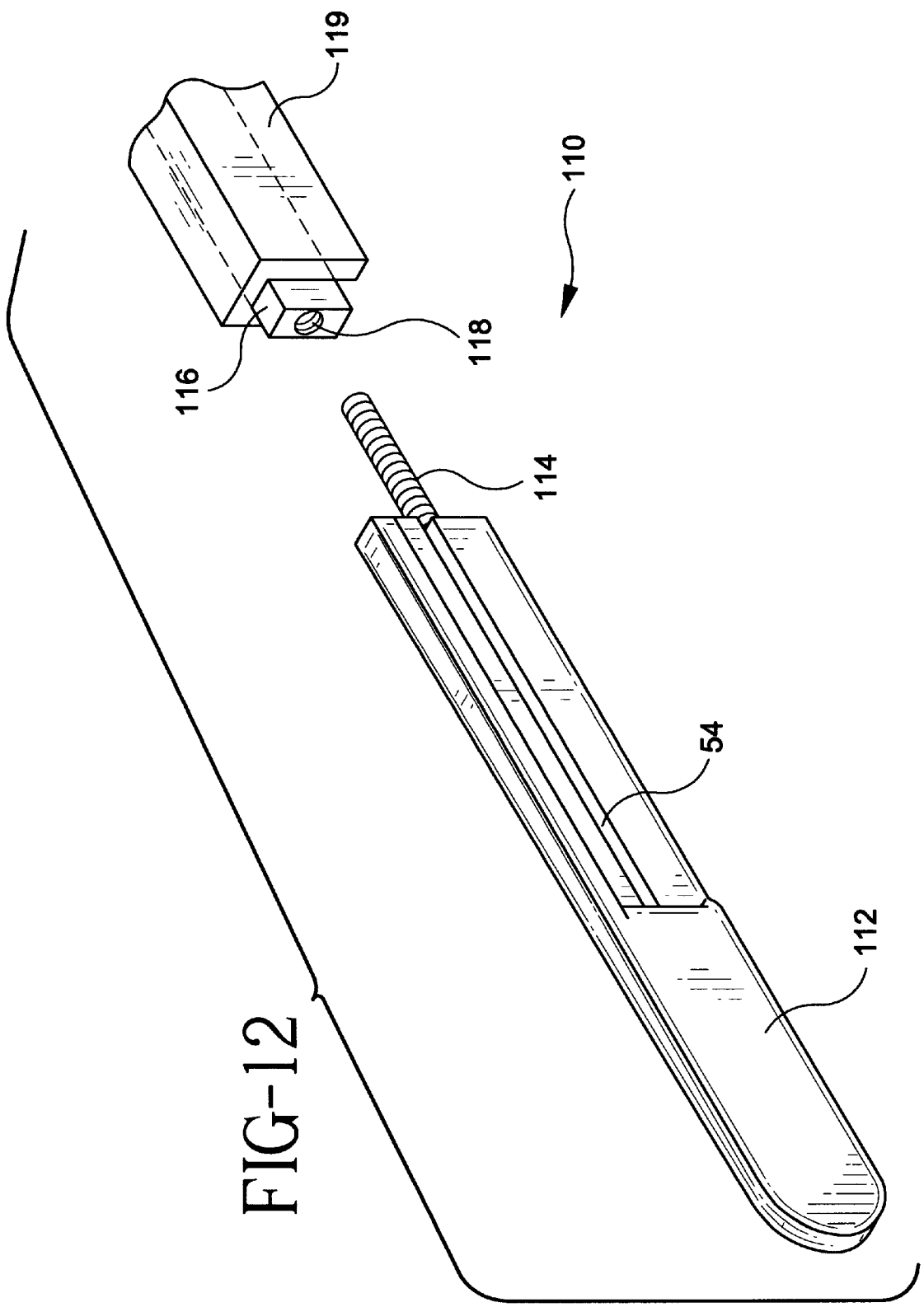

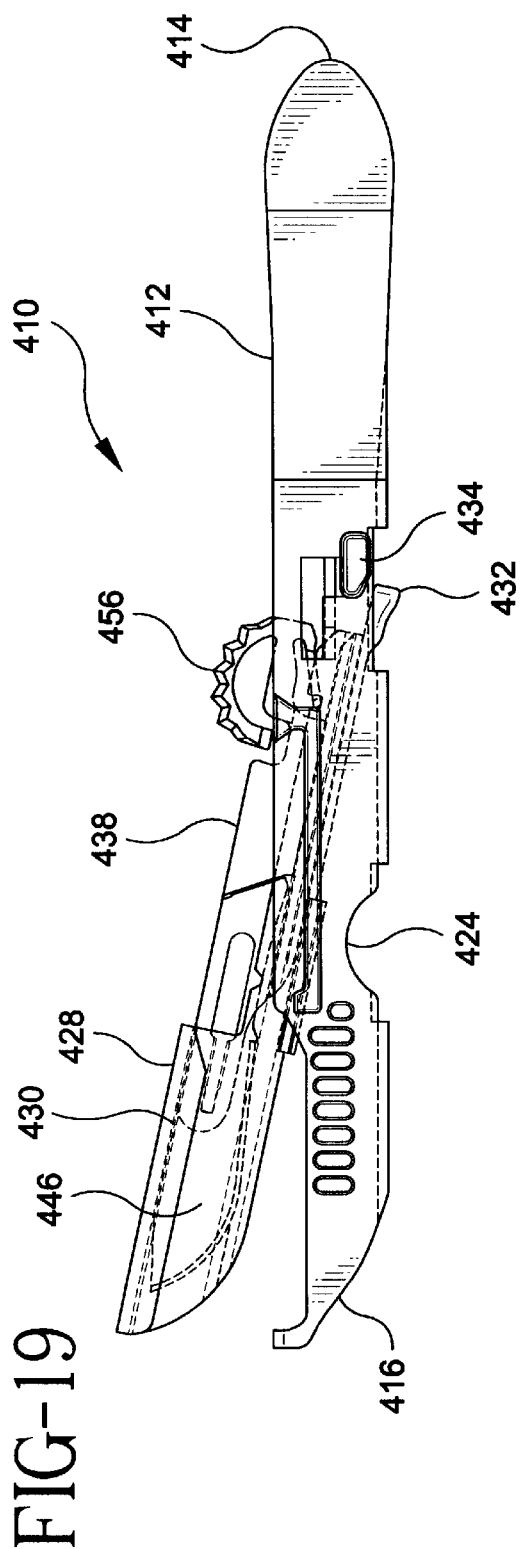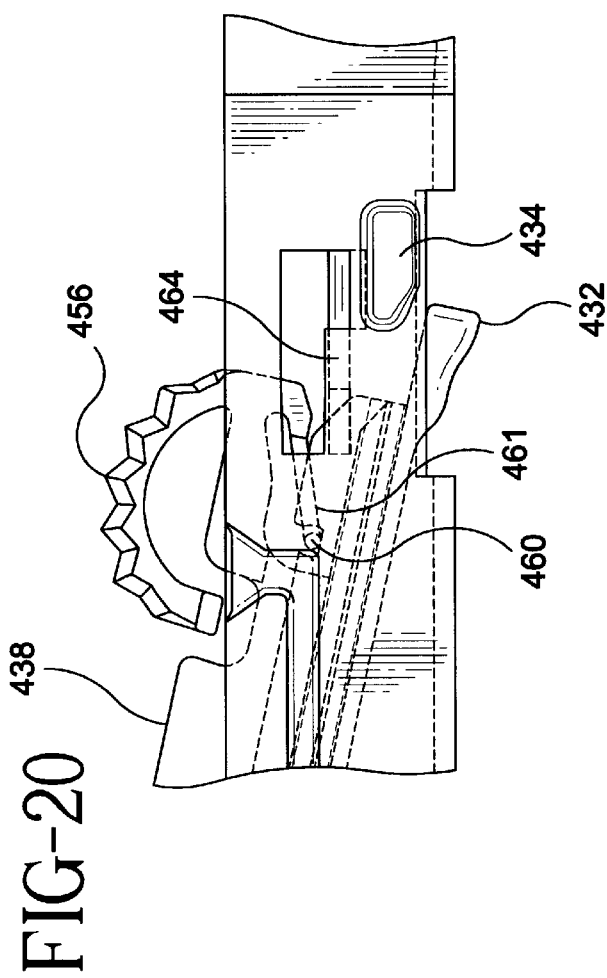

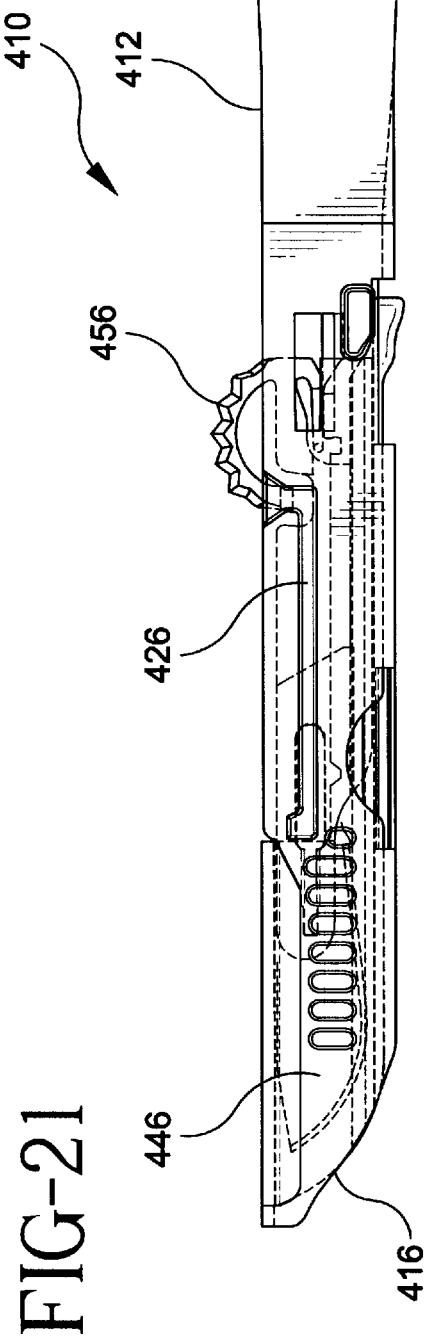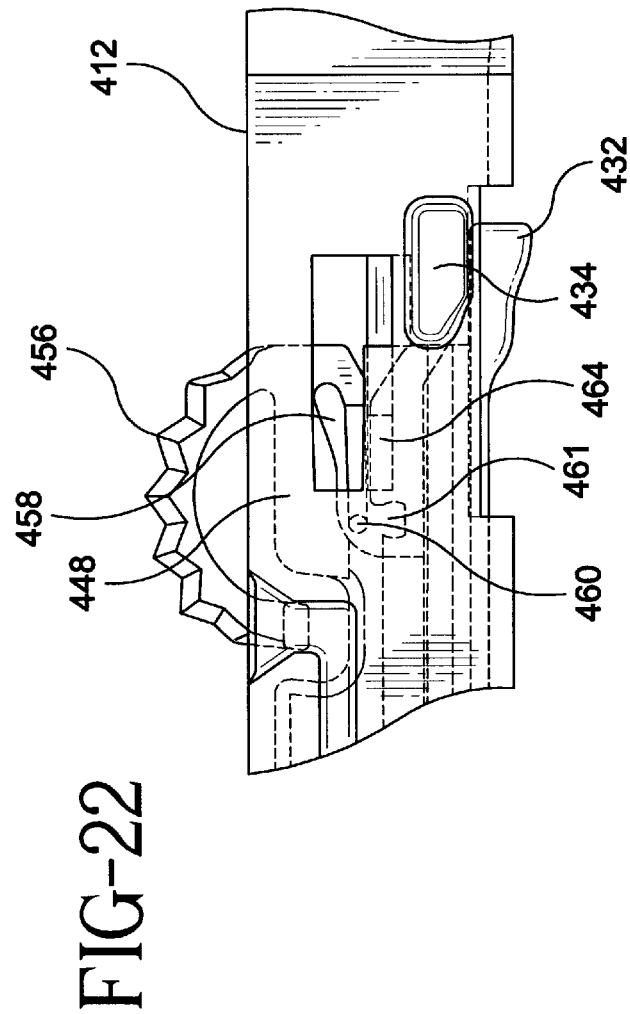

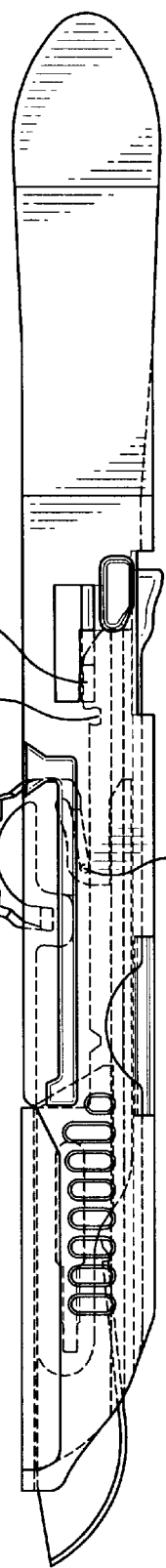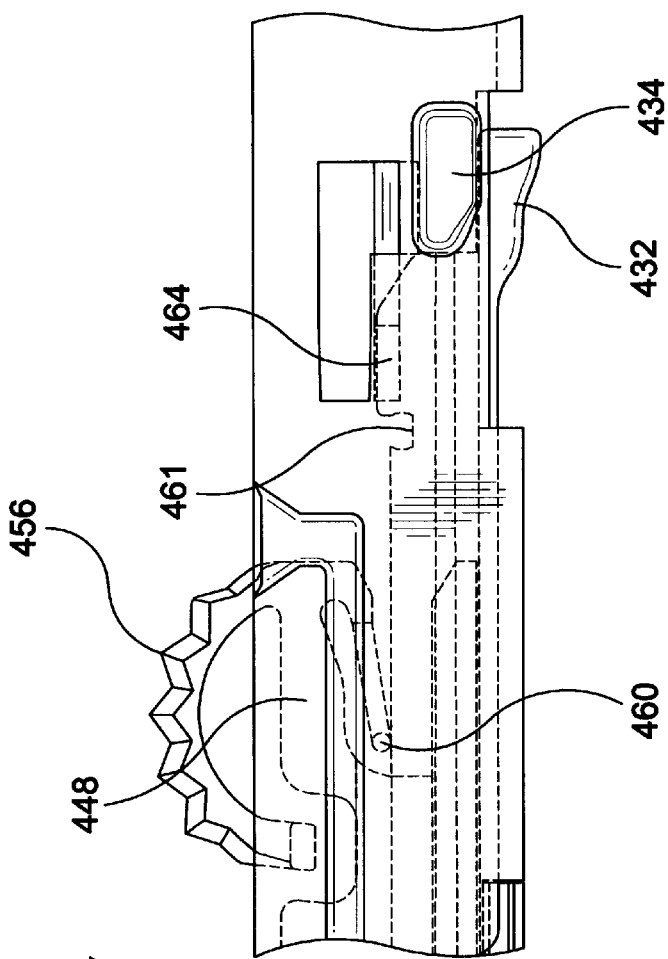
FIG-26
FIG-27

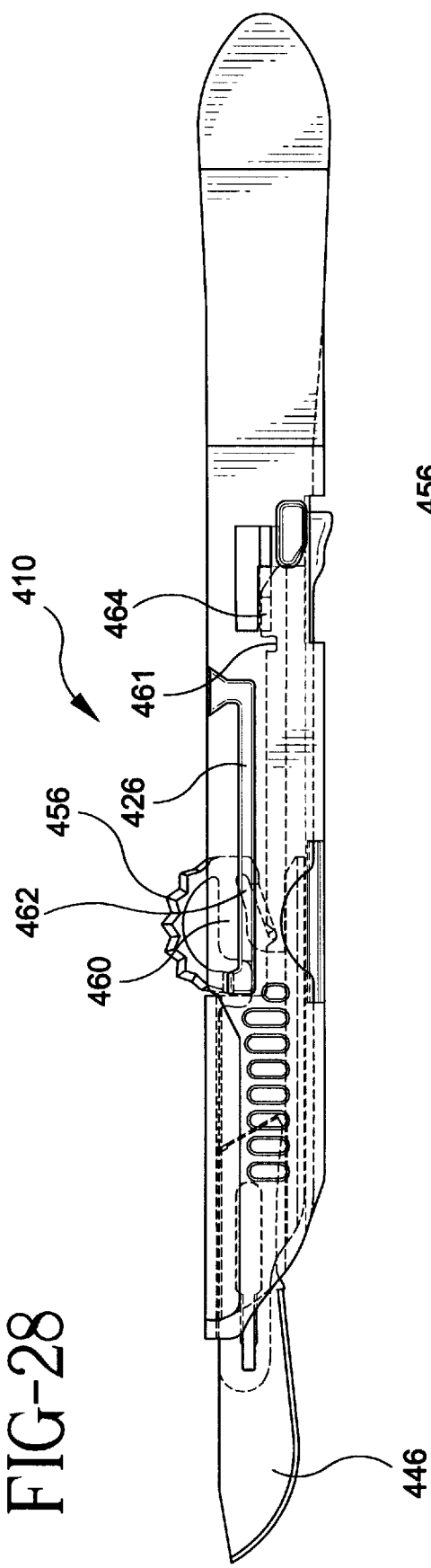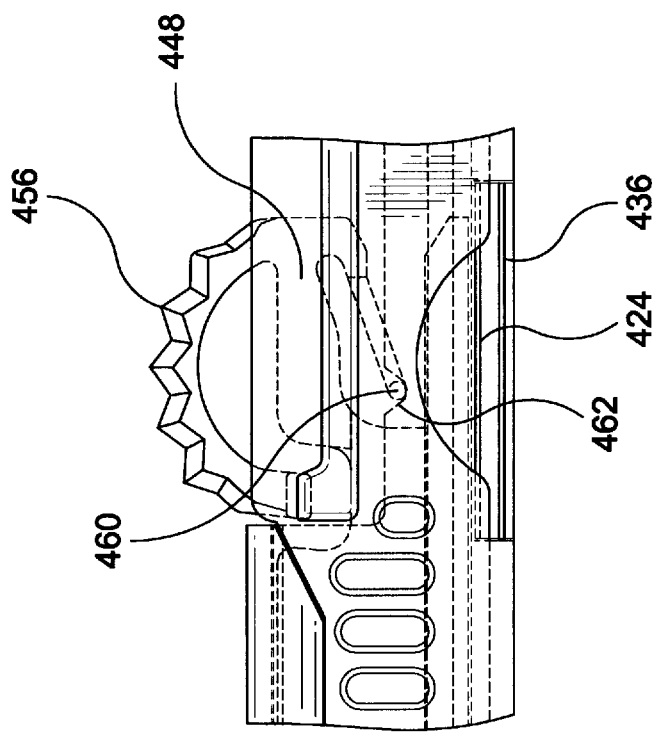

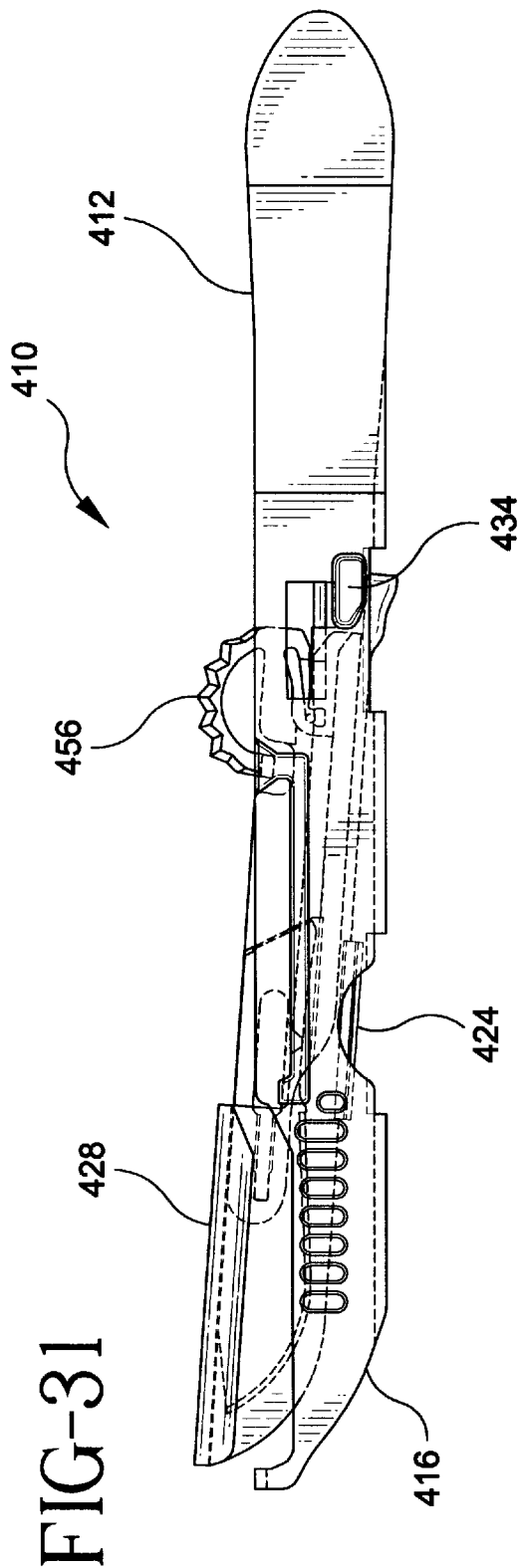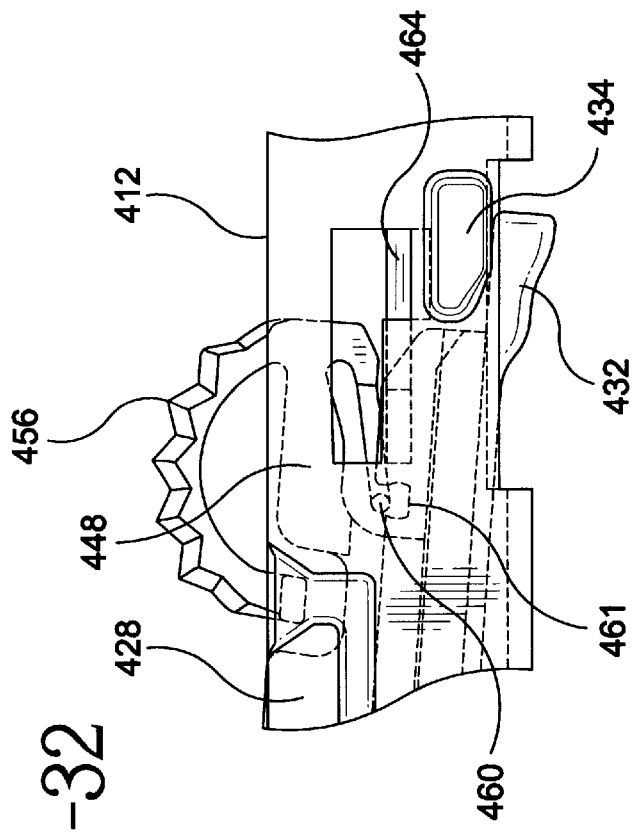

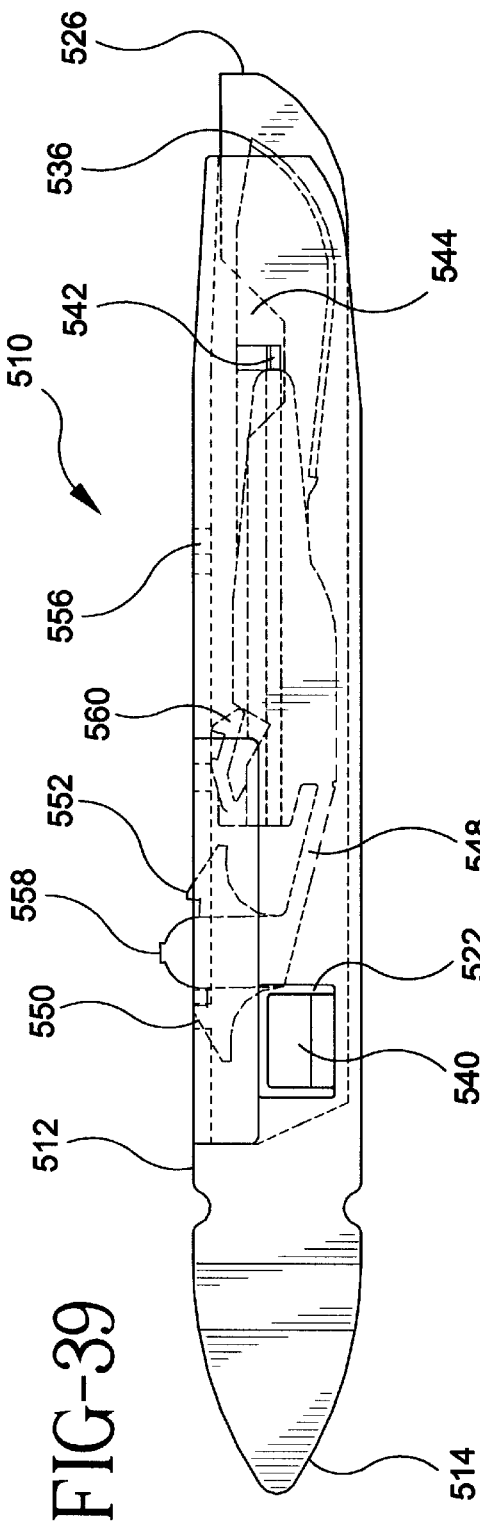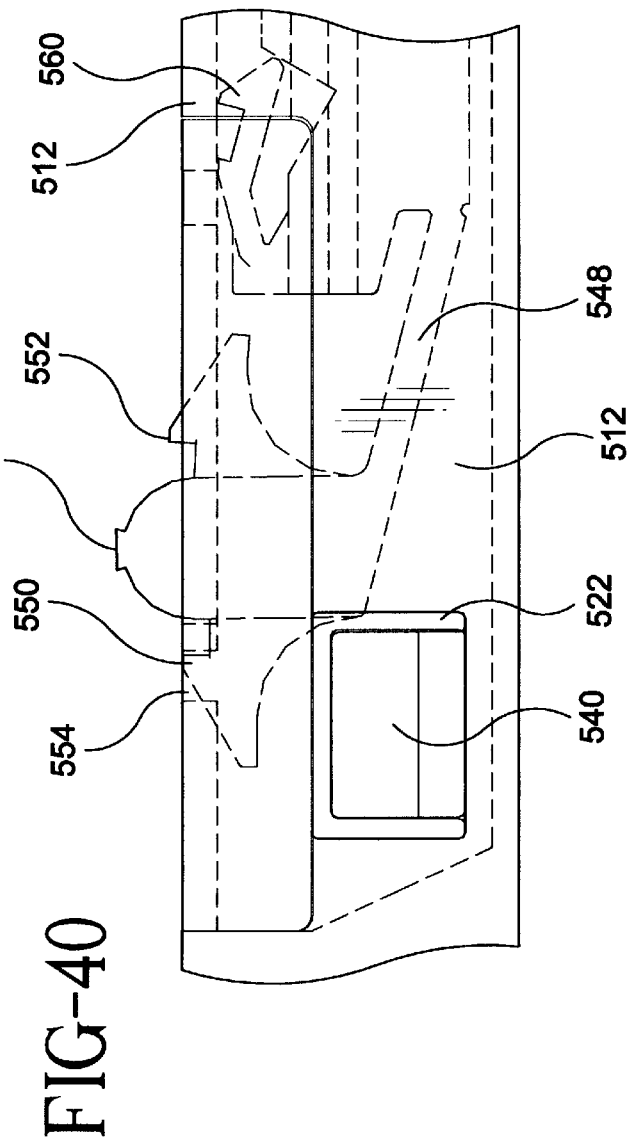
FIG-39
FIG-40

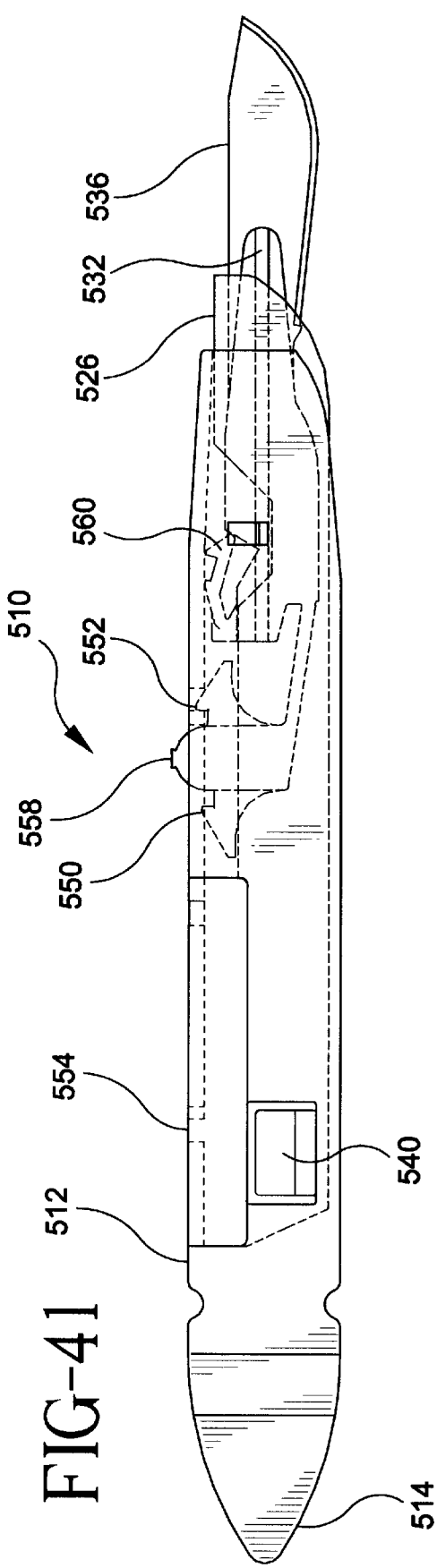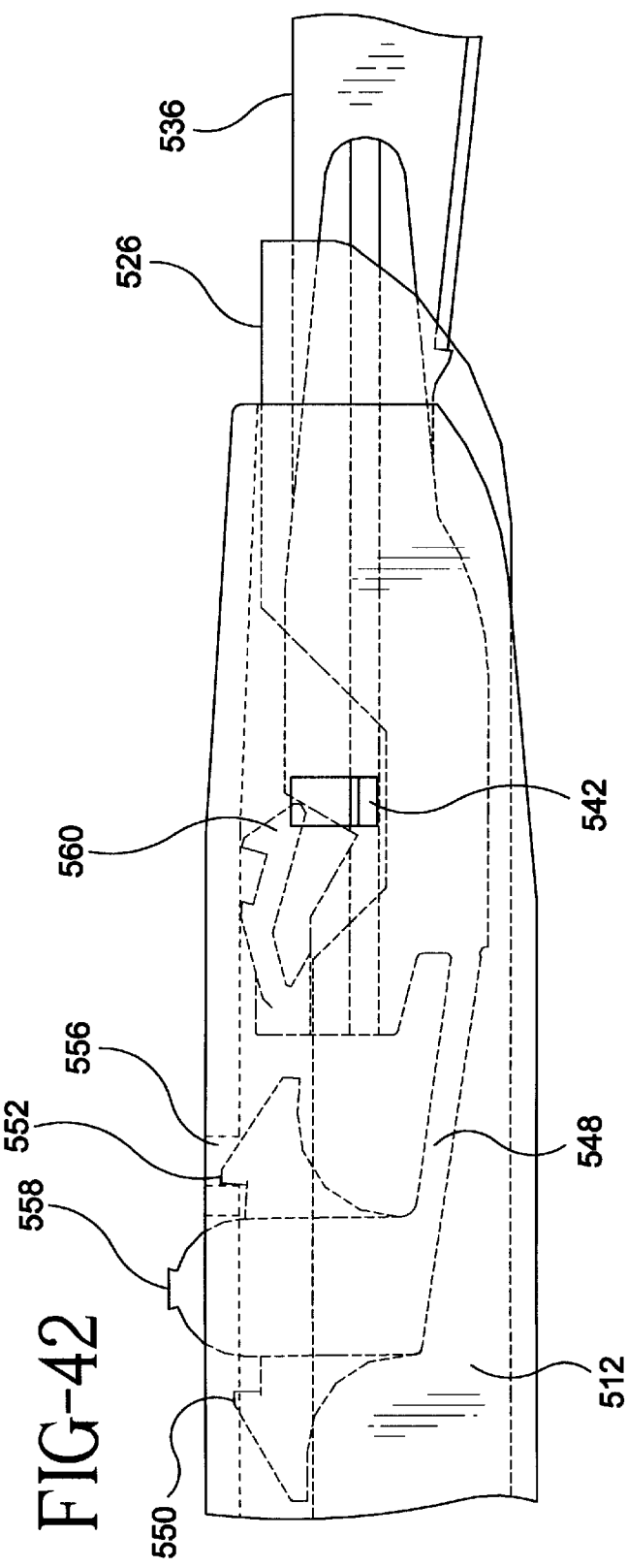
FIG-41
FIG-42

SURGICAL SCALPEL

This application is a Continuation-In-Part of U.S. patent application Ser. No. 08/666,734 filed Jun. 18, 1996, which is a Continuation-In-Part of U.S. patent application Ser. No. 08/376,065 filed Jan. 20, 1995 that is now U.S. Pat. No. 5,527,329, issued Jun. 18, 1996, which is a Continuation application of U.S. patent application Ser. No. 08/163,938 filed on Dec. 8, 1993, abandoned.

The field of the invention is surgical cutting instruments. Conventional surgical instruments provide a significant potential for harm to surgeons, nurses and other support personnel. In the operating room, various surgical instruments are quickly passed by hand. The rapid handling of such instruments with exposed sharp edges can lead to accidental cuts or puncture wounds. Surgical gloves may also be inadvertently punctured leading to loss of glove integrity further increasing the risk of infection to a surgeon, nurse or other medical personnel.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard by turning a threaded screw. Other conventional devices having spring loaded moving parts or tabs that clipped into notches on a hollow tubed sheathing device, were not practical for surgical use because they did not provide a good grip or "feel" for the blade.

SUMMARY

A surgical scalpel of the present invention includes an elongate handle that has a proximal end, an open distal end and sidewalls that define an upwardly open cavity with a bottom that has an open void therein. The sidewalls each have an elongate channel therein. The scalpel of the invention includes a cartridge that is removably retained within the cavity. The cartridge also includes a shield. The cartridge has a blade holder with a proximal end and a distal end mounted within the shield for slidable movement between a proximal and a distal position. There is a latch on the blade holder for engaging the handle and the shield to retain releasably the blade holder in the distal position and the proximal position. The scalpel of the invention has a blade fixedly attached to the blade holder so that when the blade holder is in the distal position, the blade projects distally from the handle. When the blade holder is in the proximal position the blade is within the shield and the handle and thus substantially protected from inadvertent exposure.

A surgical scalpel of the invention includes an elongate handle having a proximal end, a open distal end and sidewalls that define an open cavity therethrough, and wherein at least one of the sidewalls has an opening therethrough. The scalpel of the invention further includes a cartridge removably that is mounted within the cavity, that includes a shield. The shield releasably retains the cartridge within the cavity. The cartridge also has a blade holder with a proximal end and a distal end mounted within the shield for slidable movement between a proximal and a distal position. The blade holder has a latch for engaging the shield for releasably retaining said blade holder in the proximal position and the handle for releasably retaining the blade holder in the distal position. There is a blade fixedly attached to the blade holder disposed so that when the blade holder is in the distal position, the blade projects distally from the handle and when the blade holder is in the proximal position the blade is within the shield and the handle and substantially protected from inadvertent exposure.

The scalpel of the invention provides practitioners with a scalpel that has the feel and weighting of a traditional reusable scalpel with the benefits of a shielded fresh blade that substantially prevents inadvertent access to the sharp blade. The blade of the scalpel of the invention is intuitively movable from the proximal position where the blade is protected to the distal position to expose the blade. The replaceable cartridge allows the personnel charged with arming and disarming the scalpel to handle only a protected blade and substantially prevents operating room personnel from being inadvertently exposed to the blade during setups and transfers of equipment during procedures.

BRIEF DESCRIPTION OF THE DRAWINGS

In the drawings, wherein similar reference numbers denote similar elements throughout the several views:

FIG. 2a is a top view of the blade holder;

FIG. 2b is a side elevation view of the blade holder illustrating the position of the hook in the preferred embodiment and illustrating a partial section view of the attachment slot;

FIG. 3a is a top view of the handle shown in FIG. 1;

FIG. 3b is a side elevation view of the handle illustrating the groove and a male end attachment flange;

FIG. 4a is a top view of the sleeve;

FIG. 4b is a side elevation view thereof;

FIG. 9 is a perspective view of an alternative embodiment of the blade holder having a female end connection;

FIG. 10 is a perspective view of an alternative embodiment of the sleeve;

FIG. 11 is a perspective view of an alternative embodiment with the blade holder attached to the handle using vertical slots and tabs;

FIG. 12 is an exploded partial perspective view of an alternative embodiment with the blade holder threaded onto the handle;

FIG. 19 is a schematic side elevation of the scalpel of the invention, taken from FIG. 18;

FIG. 20 is an enlarged partial schematic side elevation of the scalpel taken from FIG. 19;

FIG. 21 is a schematic side elevation of the scalpel of the invention of FIG. 16;

FIG. 22 is an enlarged schematic side elevation of a portion of the invention taken from FIG. 21;

FIG. 26 is a schematic side elevation of the scalpel of the invention with the blade partially extended;

FIG. 27 is a schematic side elevation of a portion of the scalpel of the invention taken from FIG. 26;

FIG. 28 is a schematic side elevation of the scalpel of the invention with the blade fully extended;.

FIG. 29 is a partial schematic side elevation of a portion of the scalpel of the invention taken from FIG. 28;

FIG. 31 is a schematic side elevation of the scalpel of the invention with the cartridge partially inserted;

FIG. 32 is a partial schematic side elevation of the scalpel of the invention taken from FIG. 31;

FIG. 39 is a schematic side elevation of the scalpel of FIG. 34 analogous to FIG. 37;

FIG. 40 is an enlarged schematic side elevation of a portion of the scalpel of the invention taken from FIG. 39;

FIG. 41 is a schematic side elevation of the scalpel of the invention analogous to FIG. 38; and FIG. 42 is an enlarged schematic side elevation of a portion of the scalpel of the invention taken from FIG. 41.

DETAILED DESCRIPTION

Figure 1:
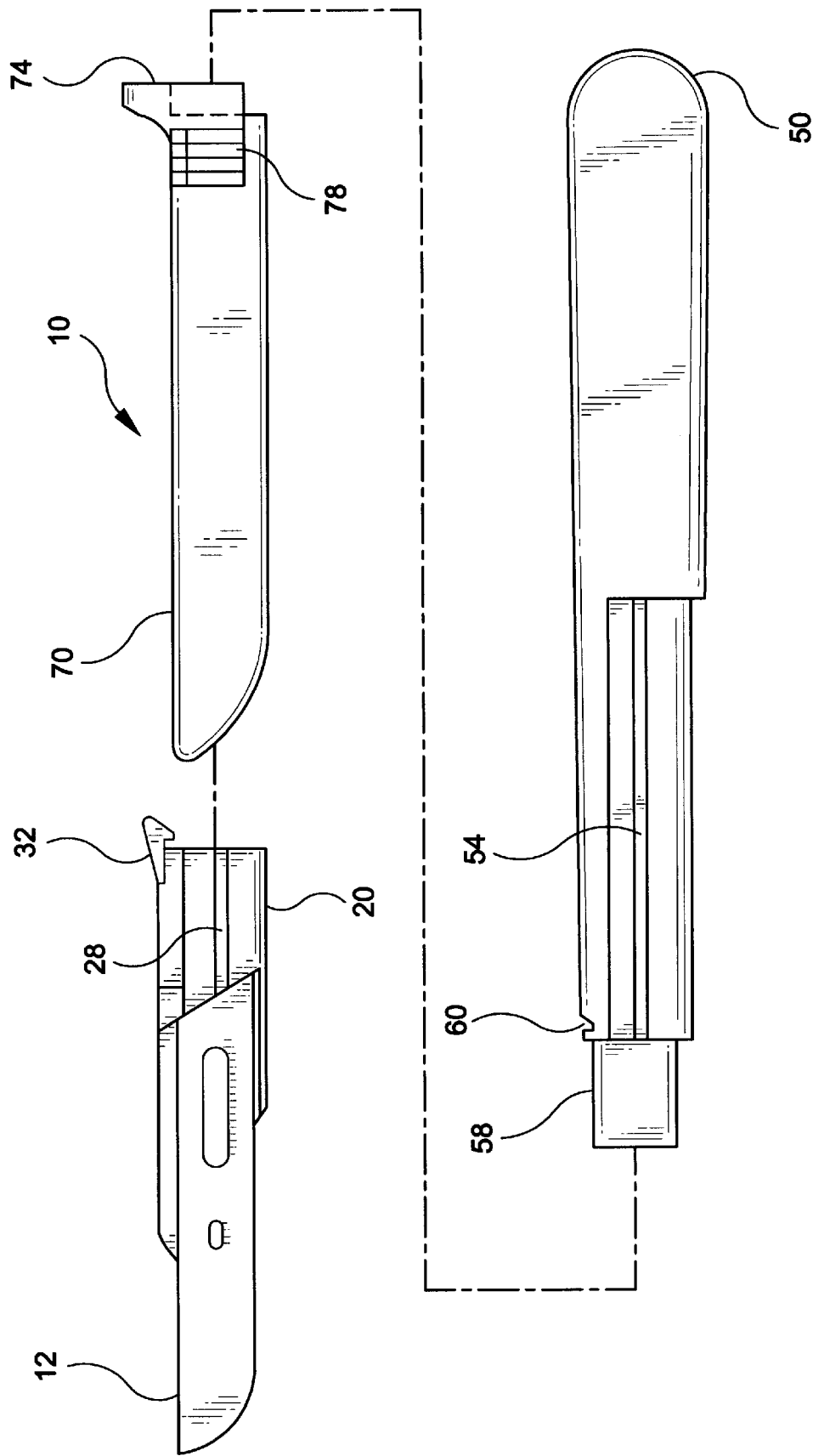
FIG. 1 is an exploded side elevation view of a preferred embodiment of the present scalpel.
Figure 2D:
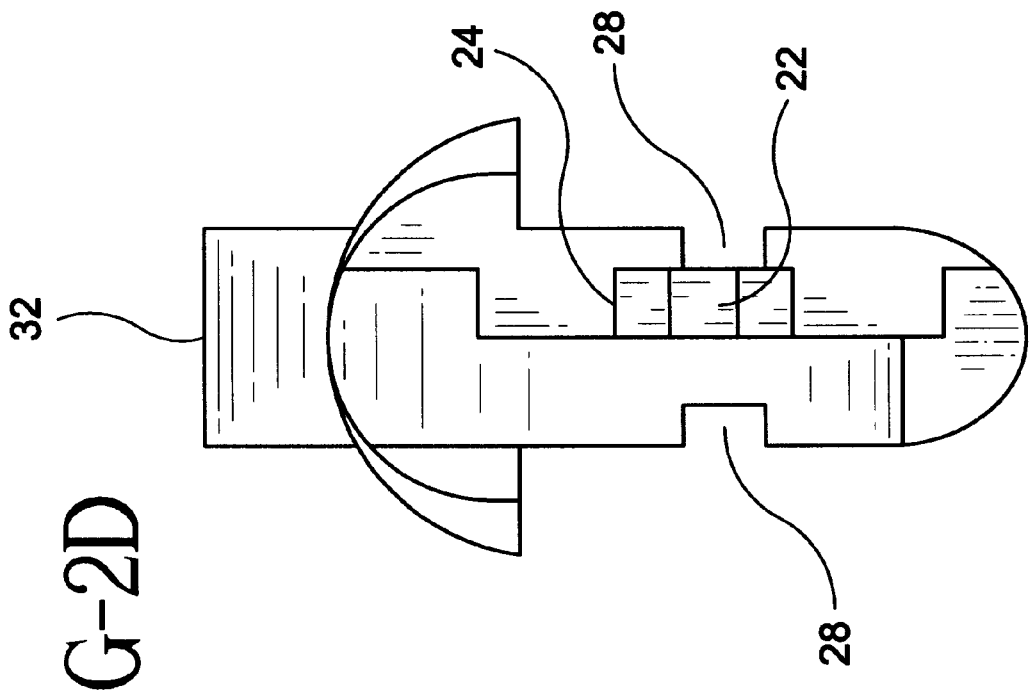
FIG. 2d is a front end view thereof.
Figure 2C:
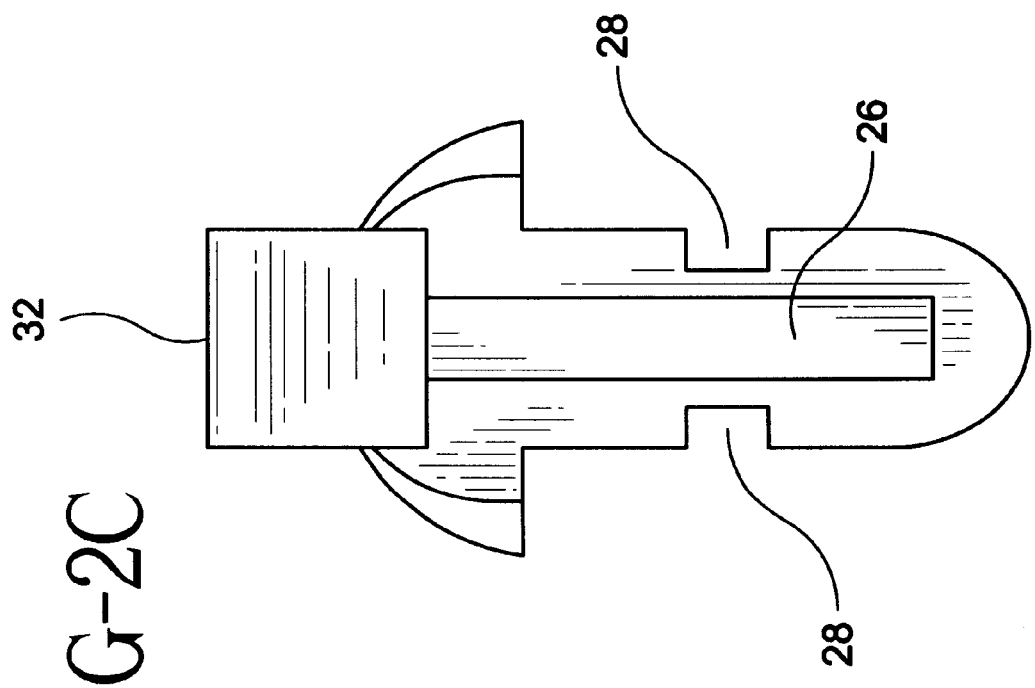
FIG. 2c is a back end view of the blade holder showing the hook and the attachment slot.

Turning in detail to the figures, the surgical scalpel 10 is first shown in FIG. 1 with the blade 12 secured to the blade holder 20. The scalpel 10 is gripped by the handle 50 which has a preferably contoured elongated grip portion 52. As is shown in FIGS. 2a and 2b, adjacent the front end of the blade holder 20 are two tabs 22 and 24 for securing the blade 12 to the blade holder 20 by interlocking with respective openings on the blade 12. Adjacent the back end of the blade holder 20 is the attachment slot 26 shown as a female end connection. Channels 28 are positioned longitudinally on opposite sides of the blade holder 20 along a channel section 30 of the blade holder 20.

A hook 32 is cantilevered from the back end of the blade holder 20. The hook 32 can resiliently flex upwardly and downwardly to engage the handle 50. The cantilevered end of the hook 32 has an inclined aft surface 34 and a protrusion 36 which is adapted to engage a complementary shaped groove 60 on the handle 50 when the blade holder 20 mates with the handle 50.

Referring now to FIGS. 3a and 3b, a pair of guide channels 54 are provided on opposite sides of the guide channel section 48 of the handle 50 in front of the grip portion 52. The guide channels 54 terminate at detents where the guide channel section 48 adjoins the grip portion 52.

Figure 3D:
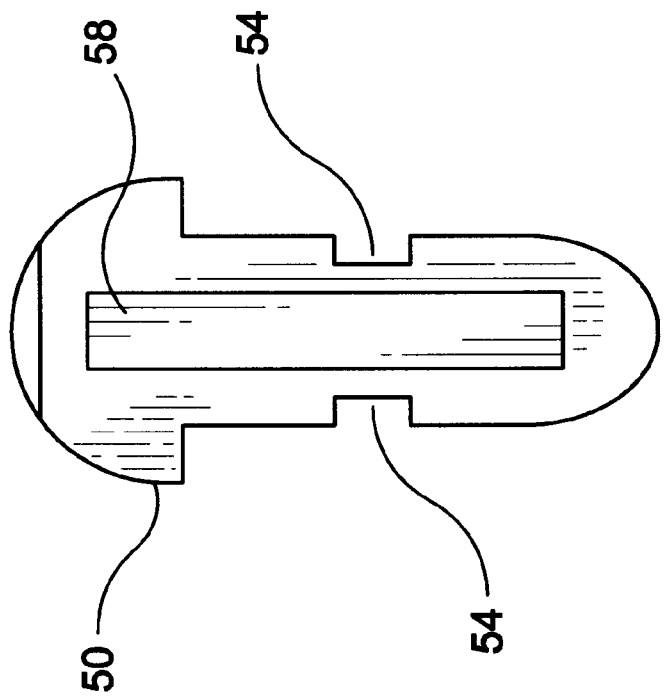
FIG. 3d is a front end view of the handle.
Figure 3C:
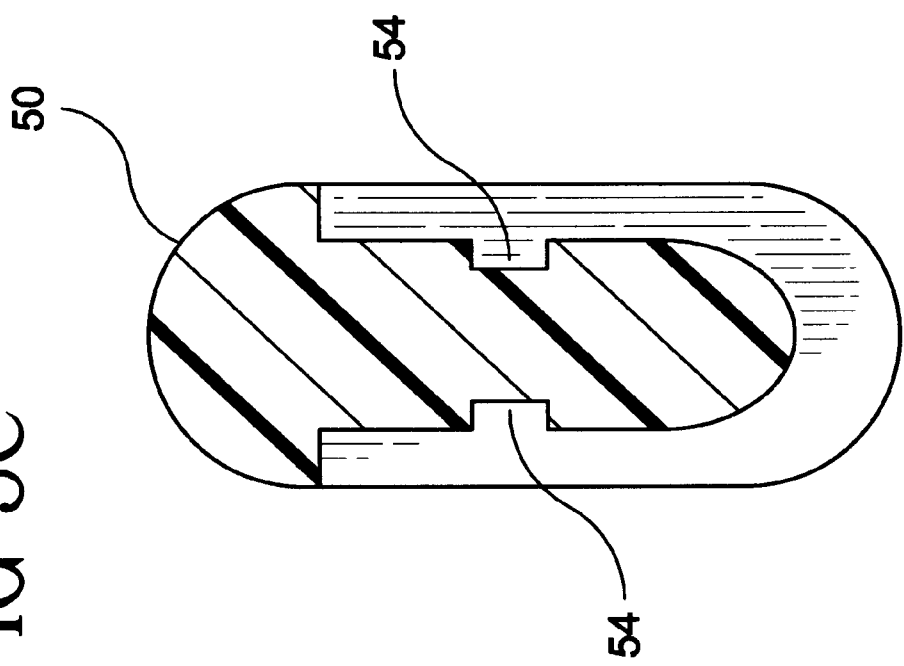
FIG. 3c is a section view taken along line 3c—3c of FIG. 3b.
Figure 4D:
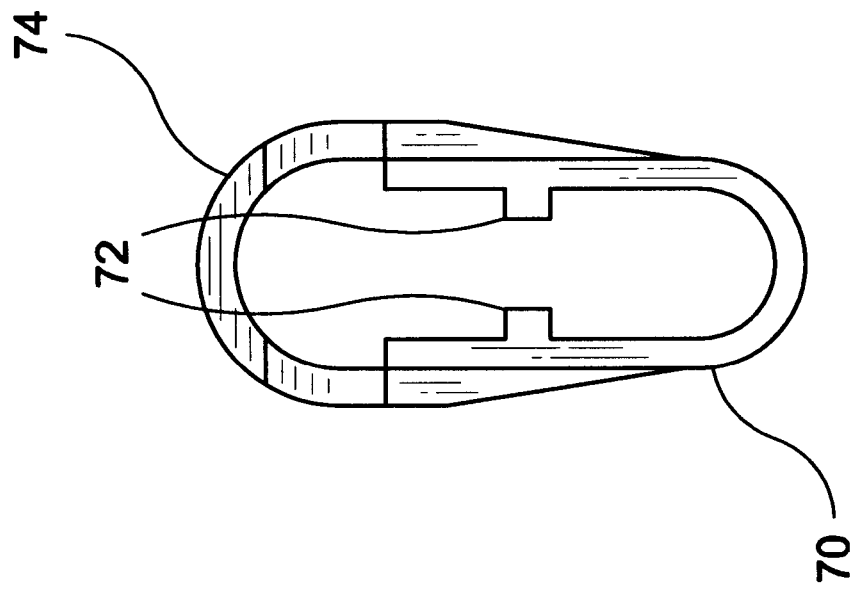
FIG. 4d is a front end view of the sleeve showing the arch.
Figure 4C:
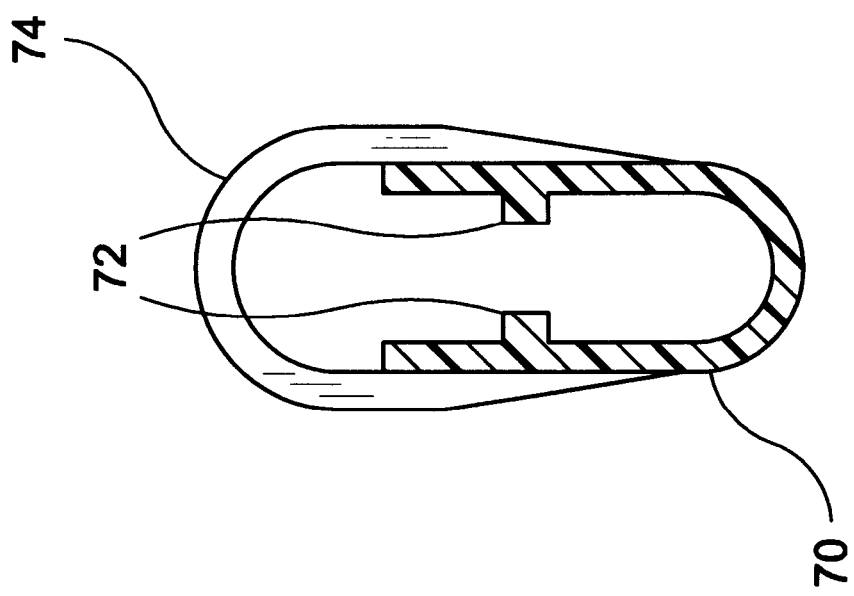
FIG. 4c is a section view of the sleeve taken along line 4c—4c of FIG. 4b.

An attachment flange 58 (shown as a male ended attachment) is joined to the front end of the guide channel section 48. As shown in FIGS. 3c and 3d, the attachment flange 58 is generally rectangular in cross section, although other configurations are possible, and is adapted to mate with the attachment slot 26 of the blade holder 20. A groove 60 at the forward end of the guide channel section 48 is shaped to mate with the hook 32.

Next referring to FIGS. 4a through 4d, the sleeve 70 is generally U-shaped in cross section having a closed bottom portion and an open upper portion. A pair of guide flanges 72 are positioned within the sleeve 70 spans between the two sides of the sleeve 70. The arch 74 preferably has a radiused front surface 76.

Figure 5A:
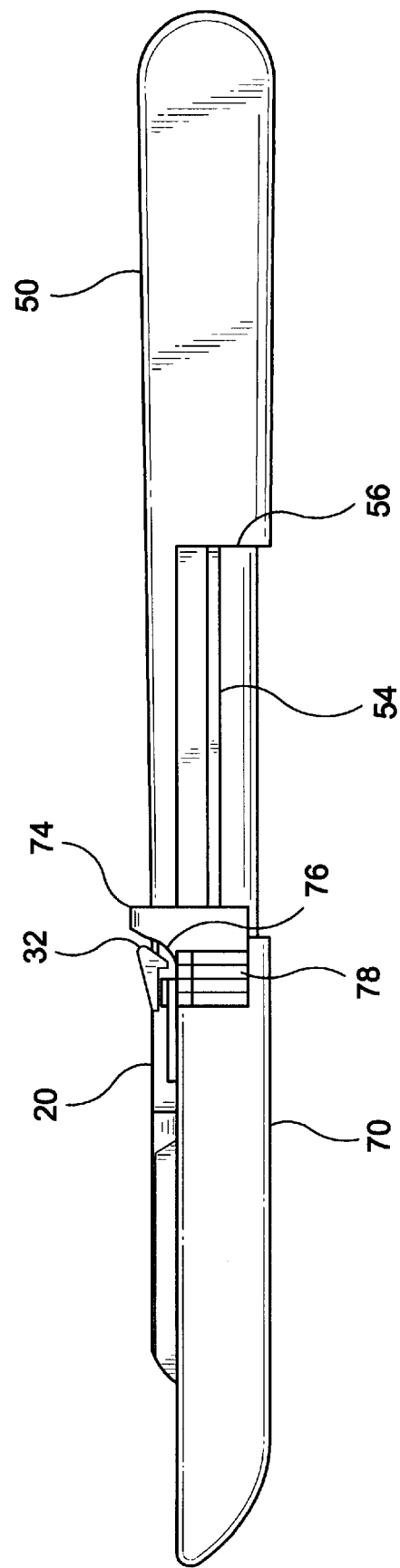
FIG. 5a is a side elevation view of the assembled scalpel with the sleeve positioned in an extended position.

The sleeve 70 preferably has a digit engaging portion 78 adjacent to the arch 74 having a series of ribs forming a thumb rest. The digit engaging portion 78 improves the surgeon's "feel" for the sleeve 70 when the sleeve 70 slides along the guide channels 28 and 54 by hand or thumb pressure. FIG. 5a shows an assembled scalpel 10 with the sleeve 70 in a forward position to cover the sheath of blade 12. The forward movement of the sleeve 70 is guided by the guide flanges 72 that travel along the guide channels 28 and 54. With the sleeve 70 moved fully forward, the radiused surface 76 contacts the hook 32 to stop additional forward movement.

Additional forward movement by the sleeve 70 toward the extended position as guided by the user's hand will cause the arch 74 to lift the hook 32 out of the groove 60 for removal of the blade holder 20 from the handle 50. This allows the sleeve 70 and blade holder 20 to be disassembled as a unit from the handle 50 while the blade 12 is sheathed by the sleeve 70, thus minimizing the risks of inadvertent cuts. The blade 12, blade holder and sleeve 70 may then be disposed of. The handle may advantageously be reused.

Figure 5B:
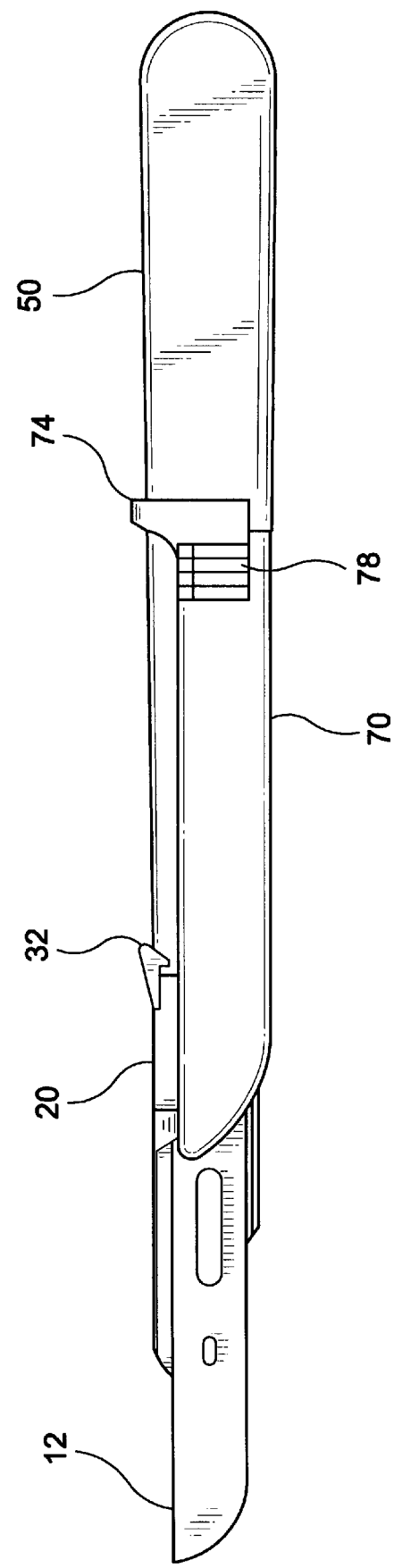
FIG. 5b is an elevation view thereof with the sleeve in a retracted position.
Figure 5C:
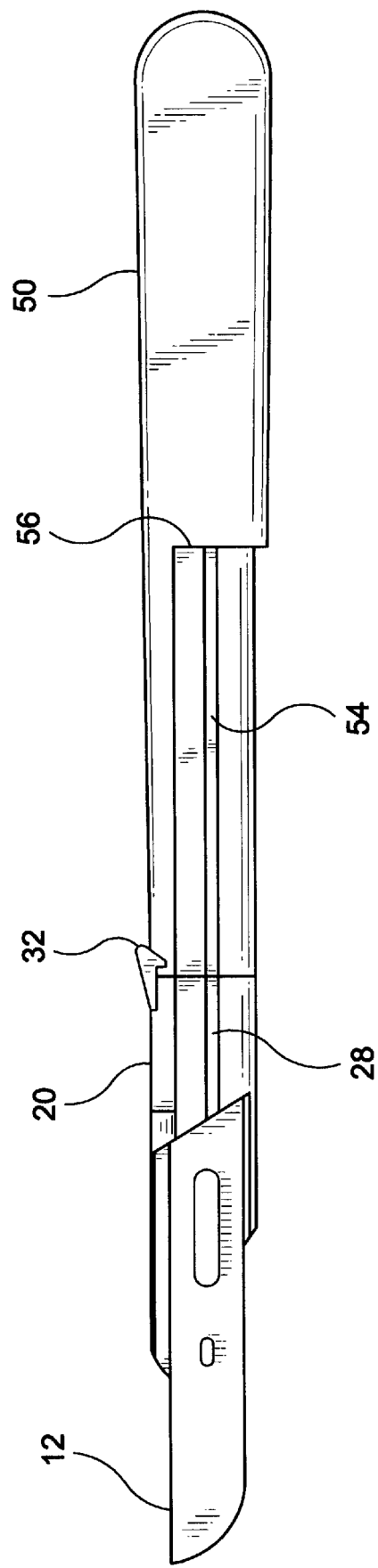
FIG. 5c is a side elevation view with the sleeve removed.

FIG. 5b shows the sleeve 70 moved to the fully retracted position with the back end of the sleeve 70 abutting the detents 56 to fully expose the blade 12. The user may utilize the digit engaging portion 78 on the sleeve 70 to improve fingertip control of the longitudinal front to back movement of the sleeve 70. FIG. 5c shows the sleeve 70 removed from the handle 50 (for purposes of illustration).

Figure 6:
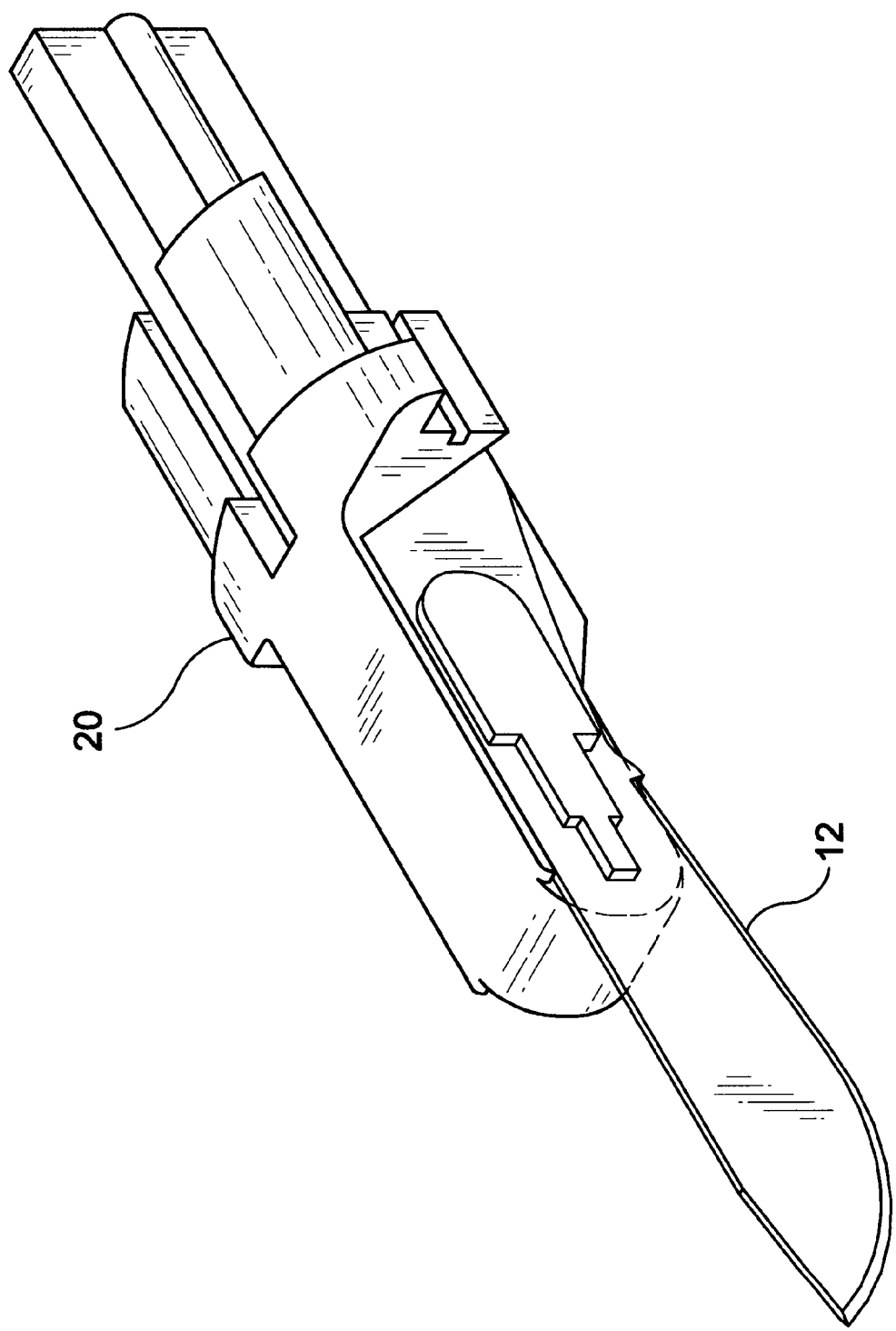
FIG. 6 shows a perspective of an alternative embodiment of the blade holder with the blade attached.

FIG. 6 illustrates an embodiment of the blade holder 20 with both a male ended attachment and a female ended slot.

Figure 7:
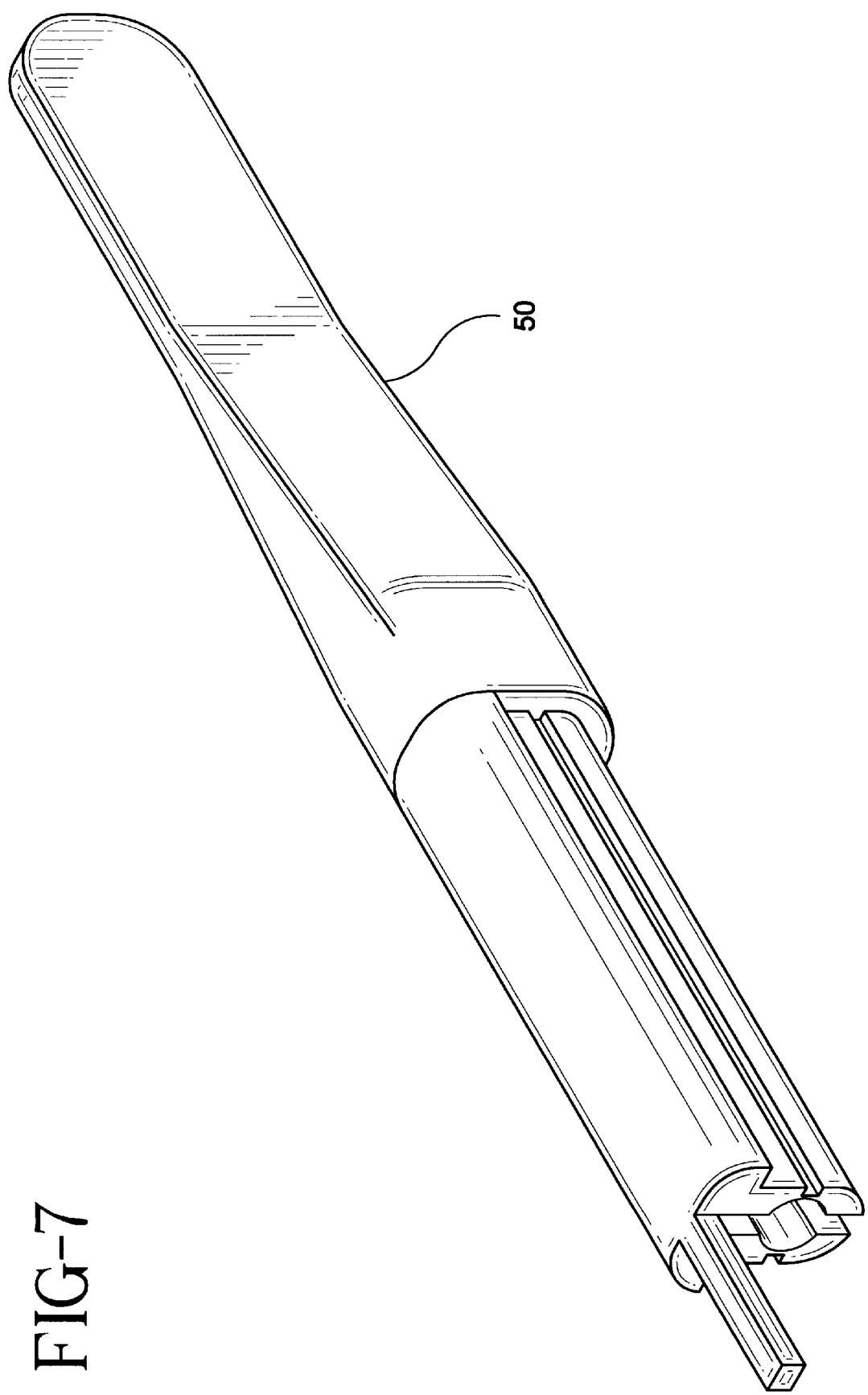
FIG. 7 is a perspective view of an alternative embodiment of the handle.
Figure 8:
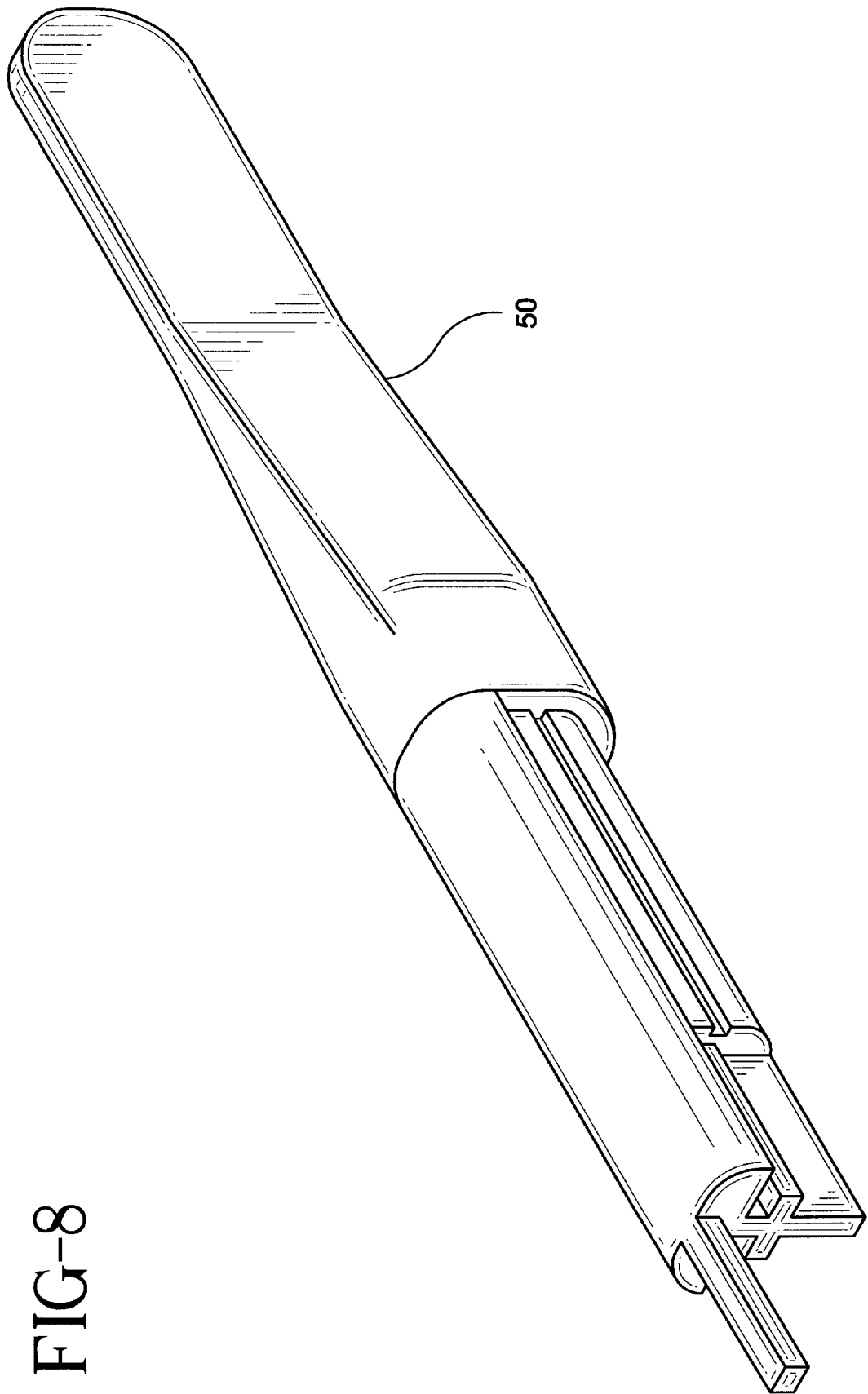
FIG. 8 is a perspective view of a second alternative embodiment of the handle.

FIG. 7 shows an embodiment of the handle 50 which mates with the blade holder 20 shown in FIG. 6. An alternative embodiment of the handle 50 is also shown in FIG. 8 with male ended connections. An embodiment of the blade holder 20 which mates with the handle 50 of FIG. 8 is further shown in FIG. 9 with an outline of the attached blade 12. An alternative embodiment of the sleeve 70 is shown in FIG. 10 which illustrates a stop tab 80 which may be utilized to stop forward longitudinal sliding of the sleeve 70. An inclined digit engaging portion 78 is illustrated and may be used to facilitate use as a thumb rest for the operation surgeon.

In an alternative embodiment 90 as shown in FIG. 11, a handle 92 has a flange 94 with vertical tabs or protrusions 96. A blade holder 98 has internal vertical slots 100 adapted to vertically slide down over the tabs 96, from above. A sleeve 102 is secured to the blade holder 98, as described above with reference to FIGS. 1–5. The sleeve 102 has a slot 104 at the back end of its lower surface. In use, the blade holder 98 is attached to the handle 92 by engaging the vertical tabs 96 into the vertical slots 100, by sliding the blade holder 98 down onto the handle 92 from above. The slot 104 in the bottom of the sleeve 102 provides sufficient clearance for the protruding vertical tabs 96.

Turning to FIG. 12, a surgical scalpel 110 has a handle 112 with a threaded stud 114 at its front end. The stud 114 threads into a threaded hole 118 at the back end of a blade holder 116. The threads on the stud 114 and in the threaded hole 118 are advantageously cut so that when the blade holder 116 bottoms out of the front end of the handle 112, the blade holder 116 will be properly vertically aligned. A sleeve 119 overlies the blade holder 116. The operation and design features of the surgical scalpels shown in FIGS. 11 and 12 are similar to the embodiment in FIGS. 1–5, except as described above.

Figure 14:
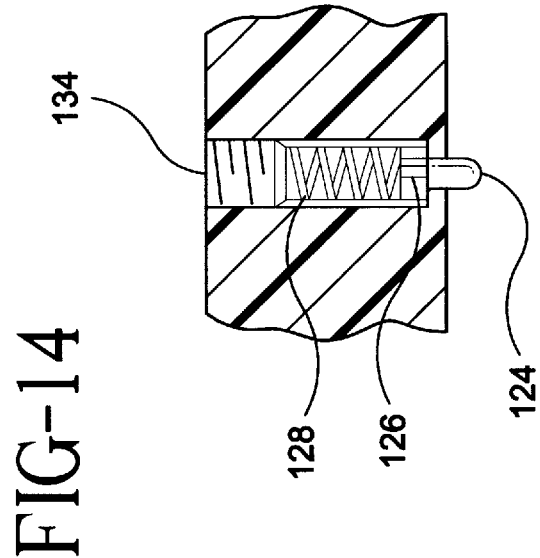
FIG. 14 is an enlarged section view of the locking button of FIG. 13.
Figure 13:
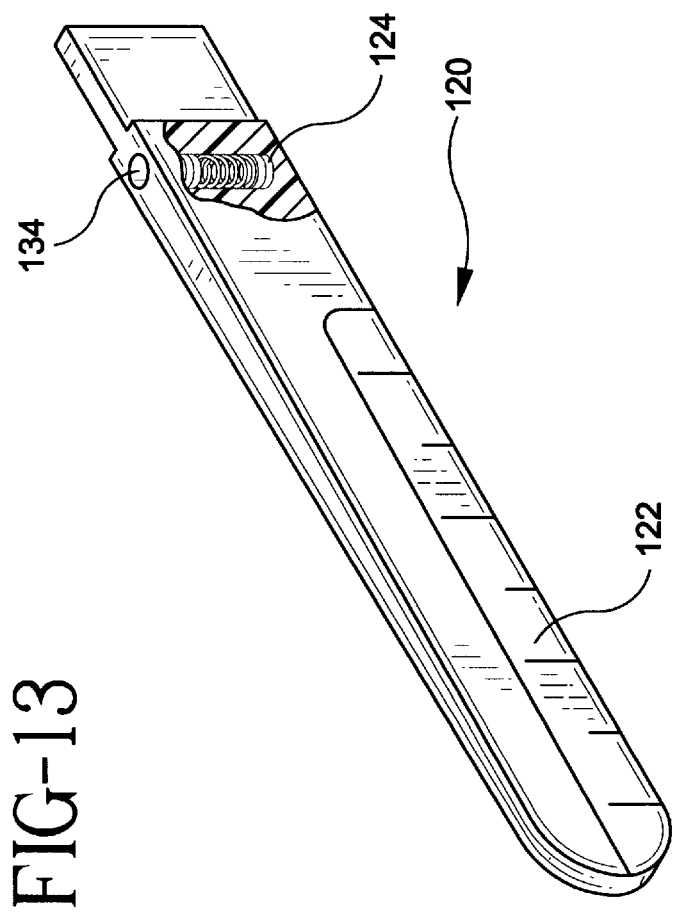
FIG. 13 is a perspective view in part section of an alternative handle embodiment having a button for locking the shield in position over the blade.
Figure 15:
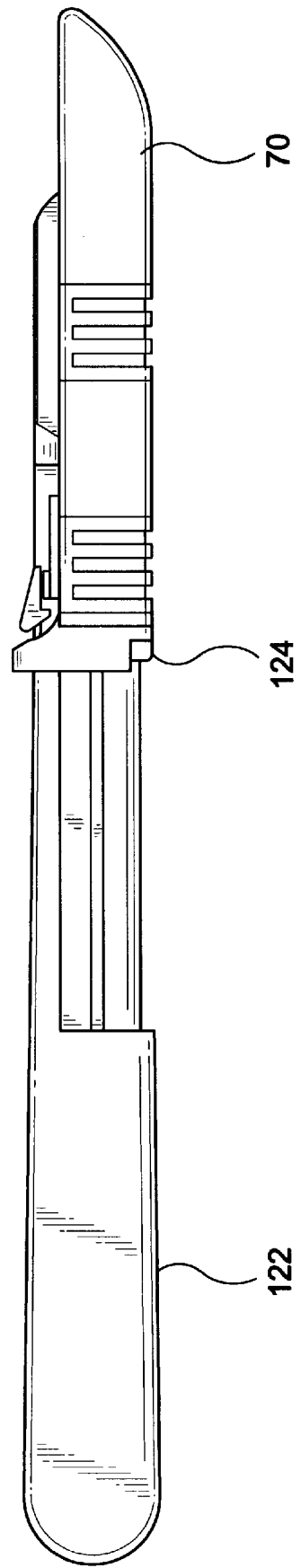
FIG. 15 is a side elevation view of the button of FIG. 14 locking the shield in its extended position.

As shown in FIG. 13 an alternative handle embodiment 122 has a locking button 124. As shown in FIG. 14, the locking button 124 has a shoulder 126 which fits within a bore 130 in the handle 122. A plug or set screw 134 at the top of the handle 122 retains a spring 128 in the bore 130, with the spring 128 biasing the locking button 124 to protrude out of the bottom surface of the handle 122. Referring to FIG. 15, with the shield 70 fully extended to cover the blade, 12, the locking button 124 protrudes out of the bottom of the handle 122. The sleeve 70 can not be retracted to expose the blade, without first pushing the locking button 124 up into the bore 130. Once the locking button 124 is pushed up into the bore 130, the sleeve 70 may be retracted, with the locking button sliding in the inside lower wall or surface of the sleeve. Accordingly, the locking button 124 helps to prevent inadvertent exposing of the blade 12. The locking button feature may be used on any of the surgical scalpel embodiments described above.

While a preferred embodiment of the present invention has been shown and disclosed in the drawings and specifications, alternate embodiments of the present invention would be apparent to the person of ordinary skill in the art and this application is intended to include those embodiments within the full breadth and scope of the claims. Moreover, the present invention need not include all of the features disclosed in the single embodiment but rather one or more features may be included.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Referring to FIGS. 16–33, a surgical scalpel 410 of the present invention includes an elongate handle 412 having a proximal end 414, a open distal end 416 and sidewalls 418 that define an upwardly open cavity 420 with a bottom 422 having an open void 424 therein. Sidewalls 418 each having an elongate channel 426 therein. As shown in the Figs, scalpel 410 includes a cartridge 428 that is removably mounted within cavity 420 that includes a shield 430. Cartridge 428 is releasably retained in cavity 420 by a proximal protuberance 432 on shield 430 that is sized and shaped to engage an inward dimple 434 in at least one, preferably both sidewalls 418 of handle 412 and a keeper 436 that is sized and shaped to engage releasably opening 424 in bottom 422 of cavity 420, when cartridge 428 is placed into the cavity. Cartridge 428 further includes a blade holder 438 with a proximal end 440 and a distal end 442 mounted within shield 430 for slidable movement between a proximal position, with respect to shield 430, best seen in FIGS. 21 and 25, and a distal position, best seen in FIGS. 28–30. Blade holder 438 has a latch 444 to engage handle 412 and shield 430 to retain releasably blade holder 438 in the distal position and the proximal position. Cartridge 428 has a keeper 436 that is disengagable from opening 424 when blade holder 438 is in the proximal position and a practitioner applies digit pressure to keeper 436, thereby to release cartridge 428 from cavity 420 as shown in FIG. 26.

Figure 25:
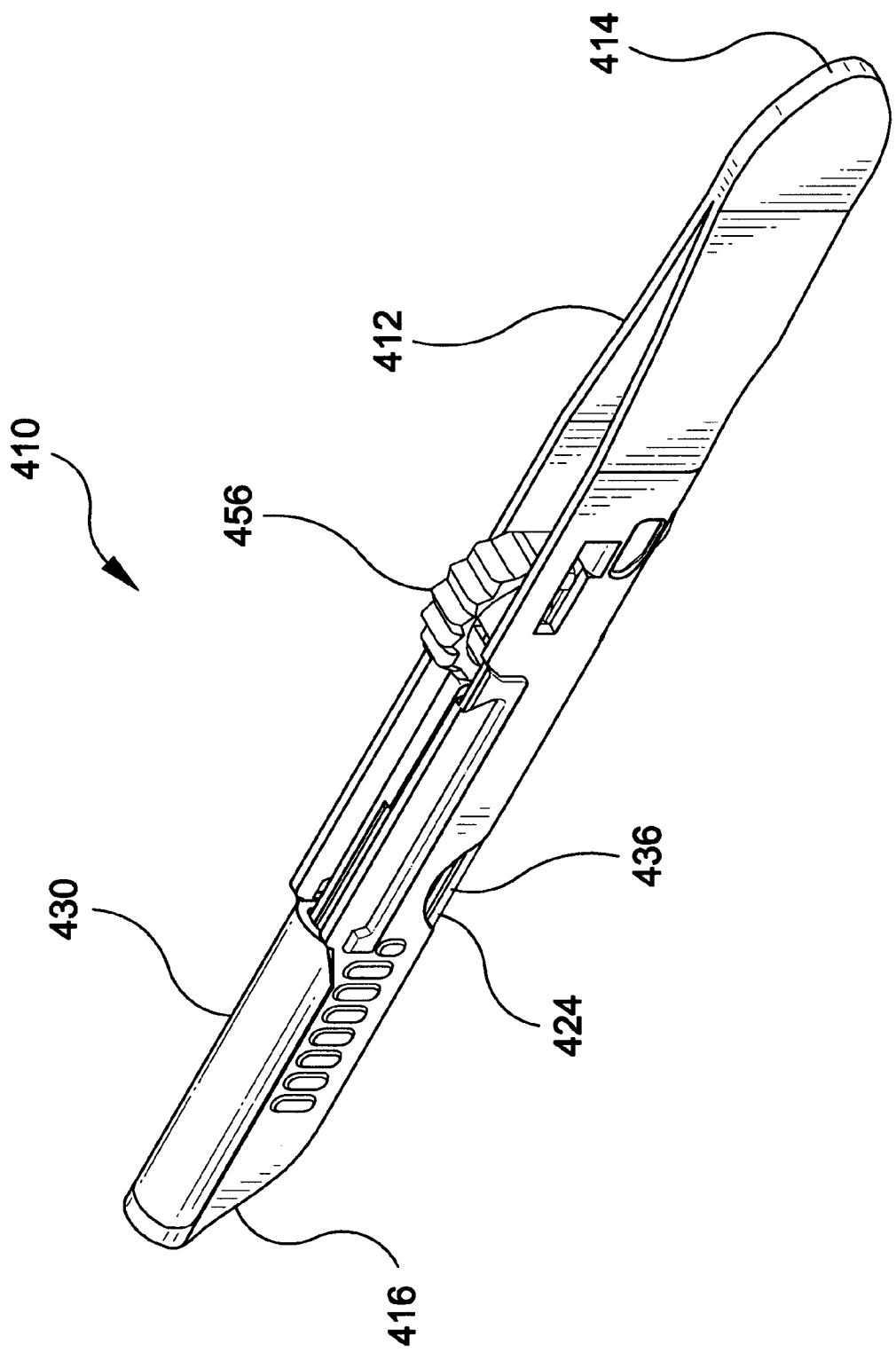
FIG. 25 is a perspective view of the scalpel of the invention.
Figure 30:
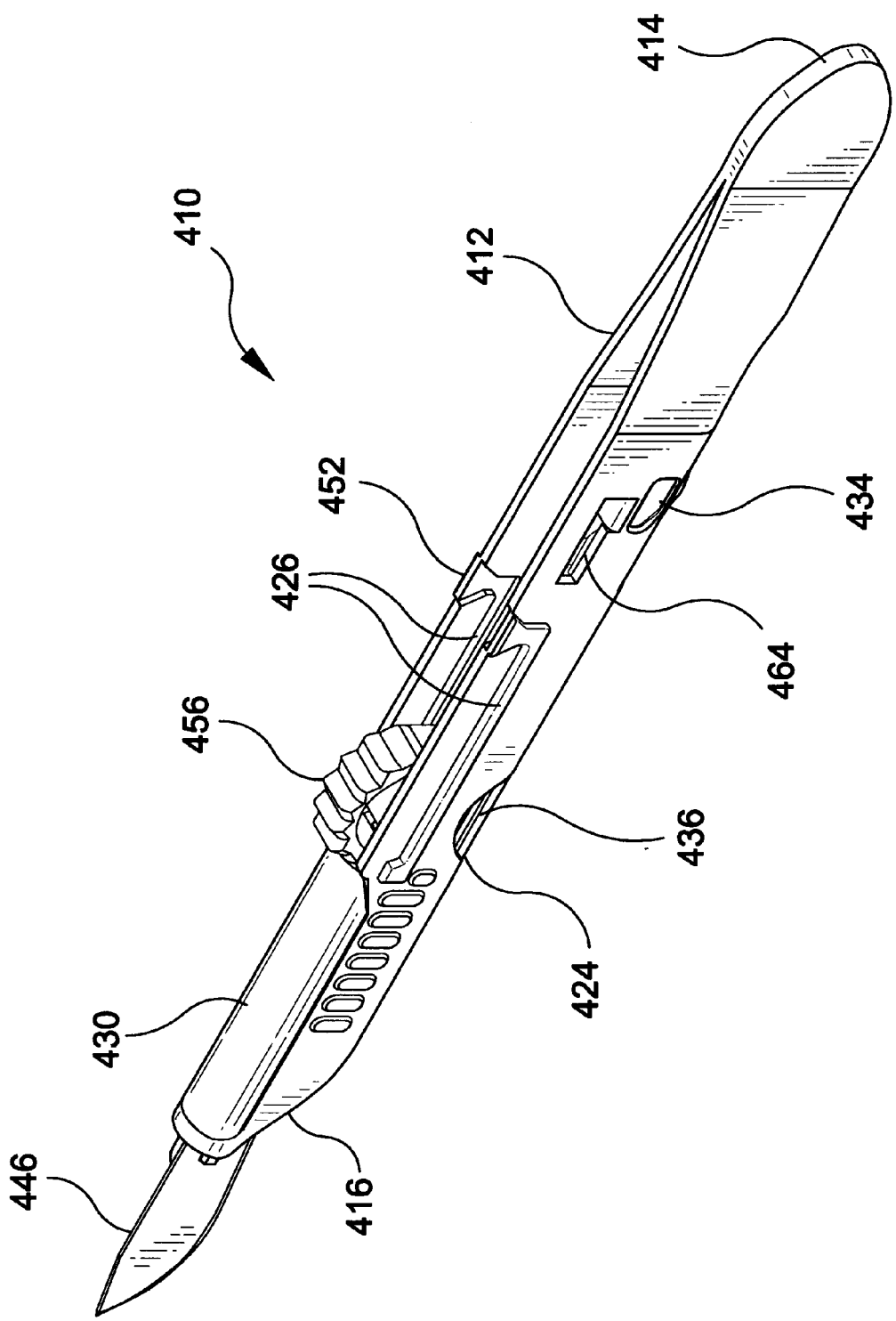
FIG. 30 is a perspective view of the scalpel of the invention with the blade extended.

Blade holder 438 has a blade 446 that is fixedly attached to blade holder 438 so that when blade holder 438 is the distal position, as shown in FIGS. 28 and 30, blade 446 projects distally from handle 412. When blade holder 438 is in the proximal position, as shown in FIGS. 21 and 25, blade 446 is within shield 430 and handle 412, thus substantially protected from inadvertent exposure.

Latch 444 engages handle 412 and releasably selectively retains blade holder 438 in the proximal and the distal positions. Latch 444 includes a first cantilever portion 448 of blade holder 438 that has at least one, preferably two, lugs 450 projecting outwardly therefrom. Lugs 450 are sized and positioned to engage channels 426 in sidewalls 418 when cartridge 428 is placed in cavity 420. Channels 426 each include a proximal stop position 452 and a distal stop position 454 for releasably retaining lugs 450 when blade holder 438 is in the proximal position and the distal position respectively. Channels 426 also serve to guide blade holder 438 between the proximal to the distal positions. Cantilever 448 further includes a digit press surface 456 that projects above handle sidewalls 418 when cartridge 428 is placed in cavity 420.

After cartridge 428 is in handle 412 with keeper 436 engaged with opening 424, a practitioner selectively moves blade holder 438 from the proximal position, where the blade is substantially protected from inadvertent exposure, to the distal position, where the blade is exposed for use, by applying sufficient digit pressure to digit press surface 456 to deflect cantilever 448 downwardly toward handle 412 and disengage lugs 450 from proximal stop position 452. When lugs 450 are disengaged from proximal stop 452, continued digit pressure by the practitioner urges blade holder 438 distally with lugs 450 following channels 426 in sidewalls 418. When blade holder 438 is fully in the distal position wherein blade 446 is exposed for use, removal of the digit pressure by the practitioner allows cantilever 448 to return to the undeflected rest position and move lugs 450 into distal stop position 454. Blade 446 is exposed for use and the blade holder is releasably latched in the distal position. The practitioner then may proceed with a procedure. When the practitioner has completed the procedure, blade 446 may be selectively withdrawn by application of sufficient digit pressure to digit press surface 456 to deflect cantilever 448 and disengage lugs 450 from distal stop position 454 and urge blade holder 438 to the proximal position. Removal of the digit pressure when the blade holder is fully in the proximal stop then allows cantilever 448 to return to the rest position and move lugs 450 into the proximal stop position to latch the blade holder proximally with blade 446 again substantially protected from inadvertent exposure. Cartridge 428 may now be removed from cavity 420 by application of sufficient digit pressure to keeper 436 to disengage it from open void 424 and lift cartridge 428 upwardly away from handle 412 so that the cartridge may be disposed of according to the institutional protocol. Cartridge 428 substantially cannot be removed from handle 412 unless blade holder 438 is in the proximal position with respect to shield 430, because lugs 450 are in channels 426. Cartridge 428 can only be removed from handle 412 when lugs 450 are in proximal stop position 452

Figure 23:
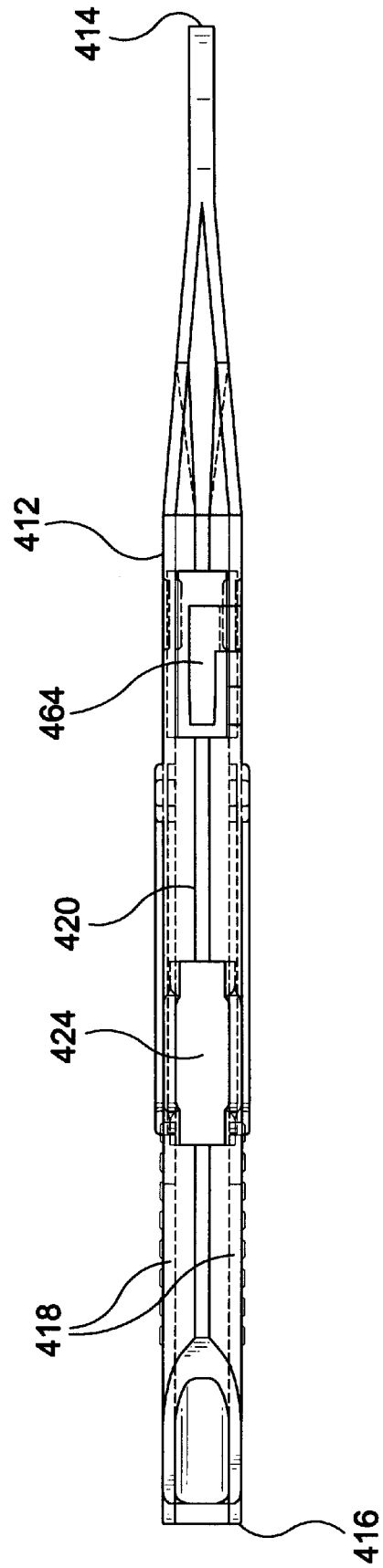
FIG. 23 is a top plan view of the handle of the scalpel of FIG. 16.

Referring to FIGS. 22, 27, 29 and 33, blade holder 438 includes a second cantilever 458 with at least one, preferably two, protuberances 460. Shield 430 has sidewalls 463 that each preferably include proximal notches 461 and distal notches 462. Protuberances 460 are sized and positioned to engage proximal notches 461 in sidewalls 463 of shield 430 when blade holder 438 is in the proximal position with respect to shield 430 and cartridge 428 is not mounted to handle 412. When protuberances 460 are engaged with notches 461, movement of blade holder 438 with respect to shield 430 is substantially prevented. As shown in FIGS. 20, 21 and 23, when cartridge 428 is mounted into cavity 420 of handle 412, a portion 464 of handle 412, best seen in FIG. 22, is sized and positioned to engage second cantilever 458, deflect it upwardly and disengage protuberances 460 from proximal notches 461, thereby allowing movement of blade holder 438 with respect to shield 430. Distal notches 462 are engaged by protuberances 460 when blade holder 438 is moved to the distal position with respect to shield 430, and serve to provide a tactile indication to the practitioner that blade holder is in the distal position with blade 446 exposed for use. Since cartridge 428 cannot be removed from the handle unless blade holder 438 is in the proximal position with respect to shield 430, protuberances 460 are engaged with proximal notches 461 and substantially prevent movement of blade holder 438 with respect to shield 430, when cartridge 428 is not in the handle, thereby substantially preventing inadvertent exposure of blade 446.

Figure 16:
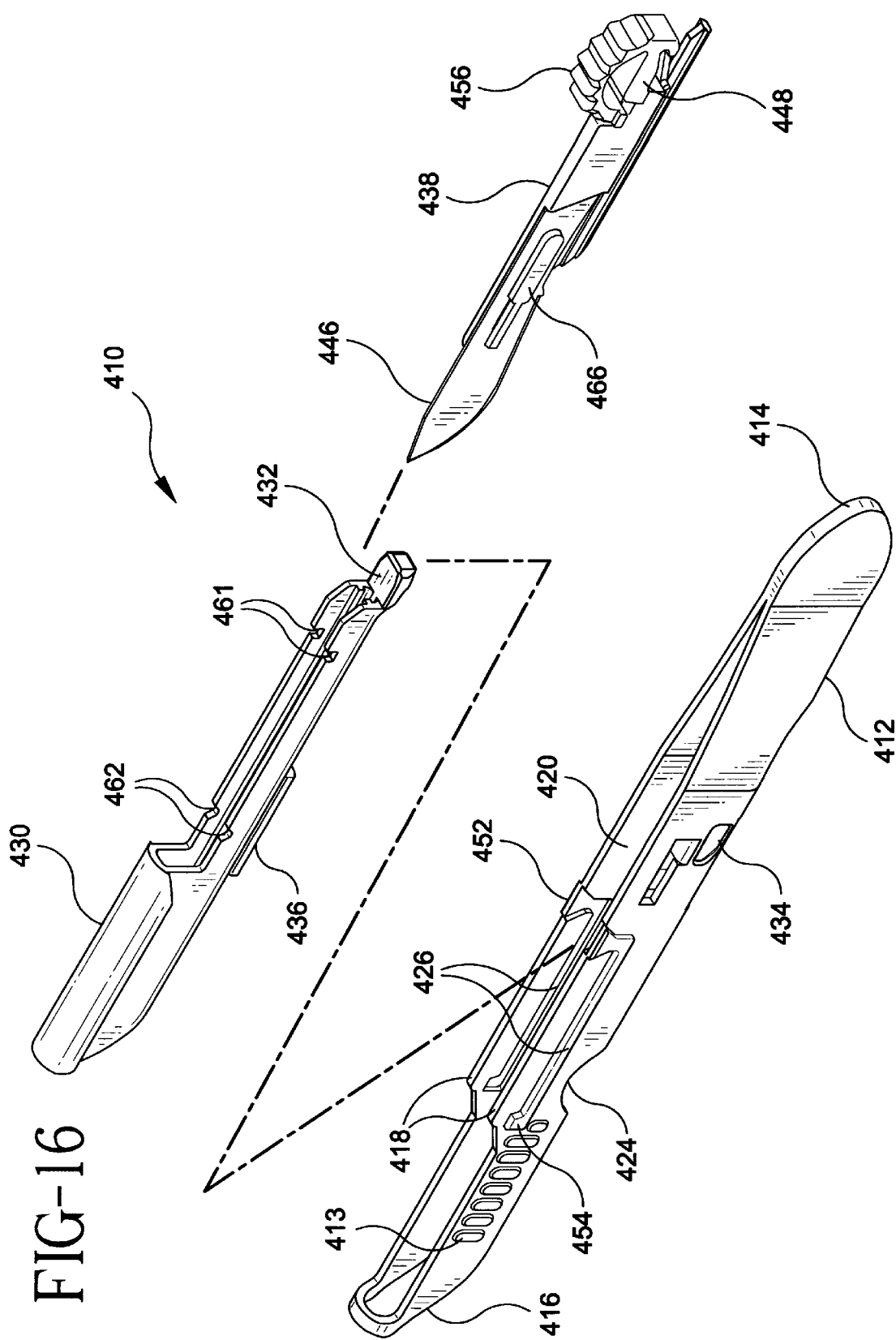
FIG. 16 is an exploded perspective view of yet another embodiment of the surgical scalpel of the invention.
Figure 17:
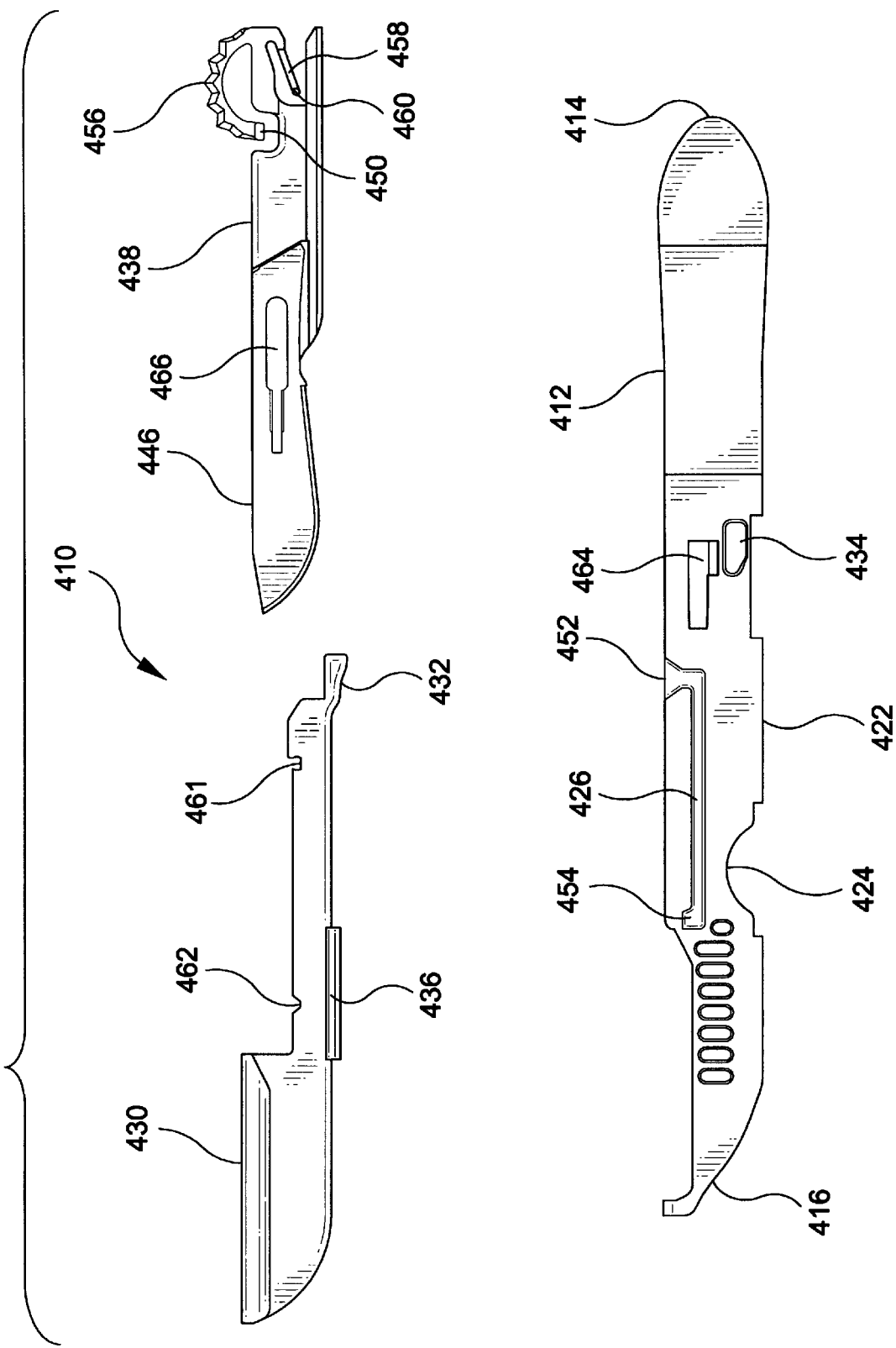
FIG. 17 is an exploded side elevation of the scalpel of FIG. 16.
Figure 18:
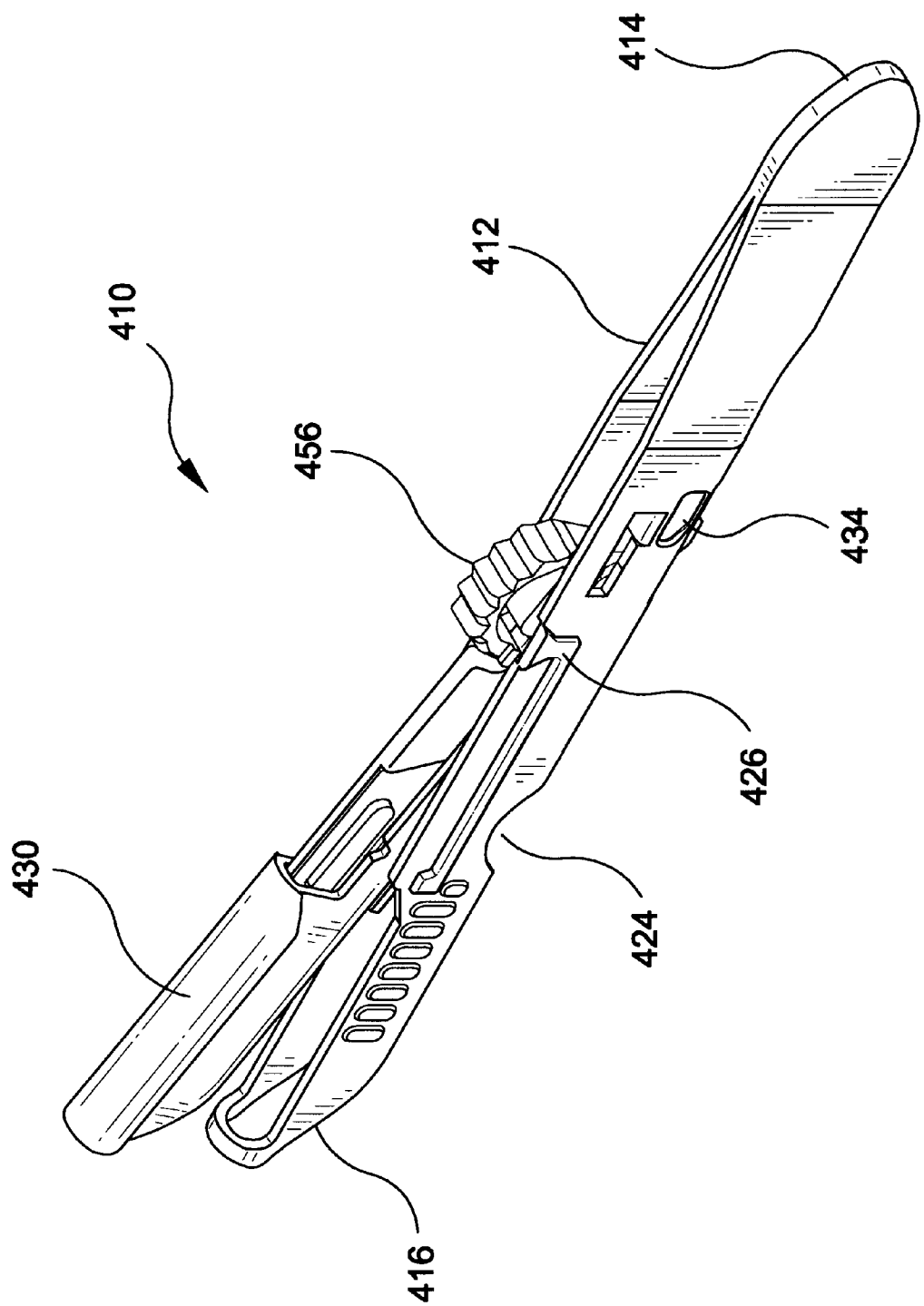
FIG. 18 is a perspective view of the scalpel of FIG. 16 partially assembled.
Figure 33:
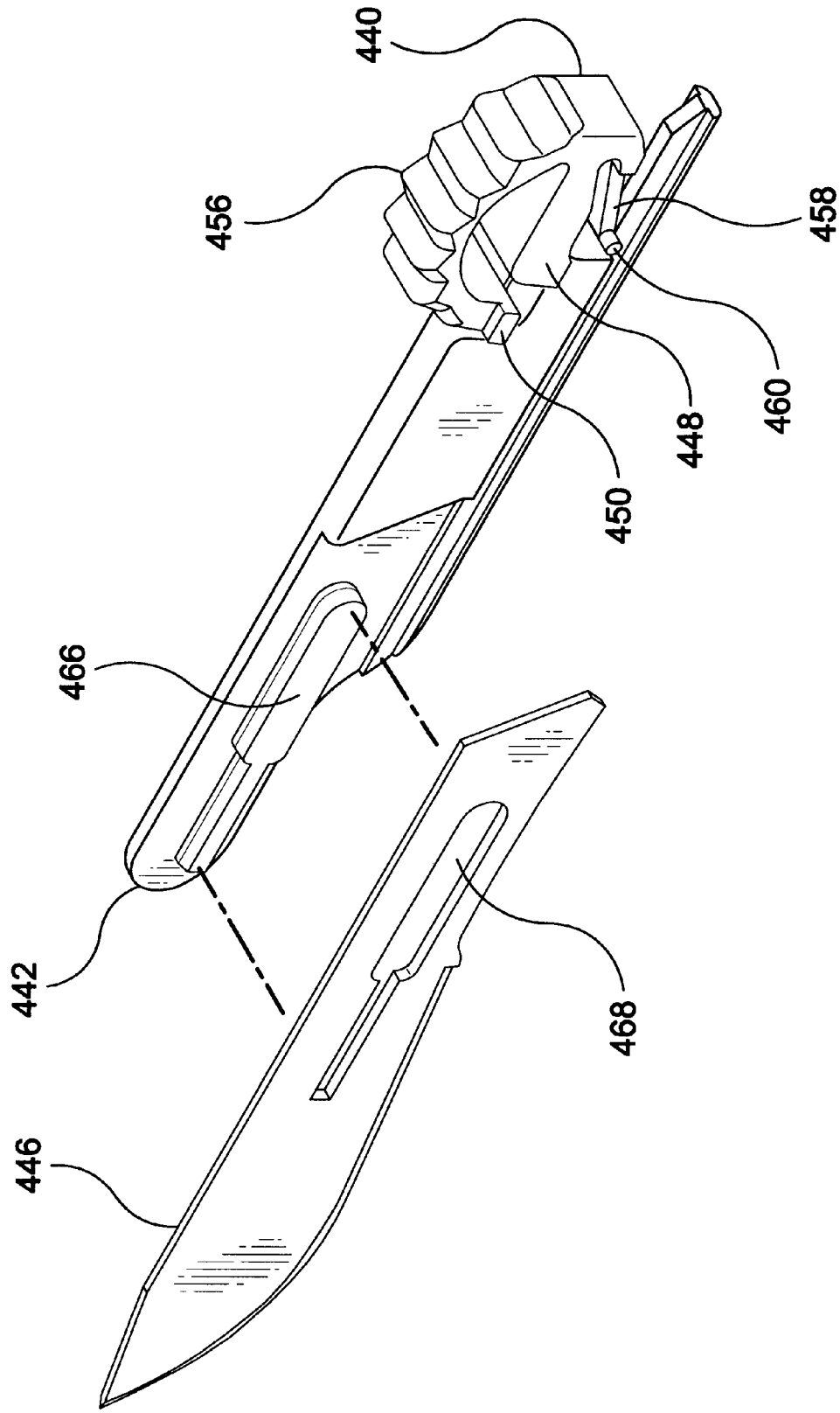
FIG. 33 is an exploded perspective view of the blade holder from the scalpel of the invention in FIG. 16.

Referring to FIGS. 16 and 33, blade holder 438 includes an outward projection 466 sized and shaped to fit an aperture 468 in blade 446 for mounting blade 446 to the blade holder. Blade 446 may be fixedly attached to the blade holder 438 by heat staking, adhesive bonding or any other type of attachment known to be satisfactory for forming such an attachment. It is the intention of the invention that blade 446 not be removable from the blade holder without rendering the blade holder substantially non-functional. Preferably, blade 446 is fixedly attached to blade holder 438 by a heat staking process to provide the fixed and substantially rigid attachment of the blade that is required by practitioners. Blade 446 may be any size or shape blade commonly used for surgical procedures and formed from any materials commonly used for such blades. Preferably, blade 446 is formed from a stainless steel and sharpened to a fine cutting edge. Handle 412 preferably has a surface treatment, here illustrated as knurling 413, to improve the practitioner's ability to securely grip the scalpel. Other surface treatments including roughening, grooving, checkering and the like may be preferred for particular applications and are considered within the scope of the invention.

Blade holder 438 may be formed from thermoplastic materials such as polypropylene, polyethylene, polycarbonate, polysulfone, polyacetal, polyamide and the like. Shield 430 may be formed from thermoplastic materials such as polypropylene, polyethylene, polysulfone, polycarbonate, polyacetal, and polyamide and the like. For particular applications shield 430 may be formed from a substantially transparent material. Handle 412 may be formed from a material such as machined metal, formed powdered metal and thermoplastic or thermoset materials. In the preferred application, shield 430 and blade holder 438 are formed from thermoplastic materials such as polypropylene and polycarbonate with a stainless steel blade to form the single-use cartridge 428. Preferably, handle 412 is formed from sheet stainless steel formed by a stamping process to provide a durable reusable device that provides the practitioners with the same "feel" and "heft" that they are accustomed to with the current reusable handles and with removable single-use bare blades. Handle 412 preferably has a surface finish 413, here illustrated as knurling, to improve the practitioner's ability to grip the handle. Other known surface finishes known to improve gripping ability may be selected and are considered within the scope of the invention.

Figure 24:
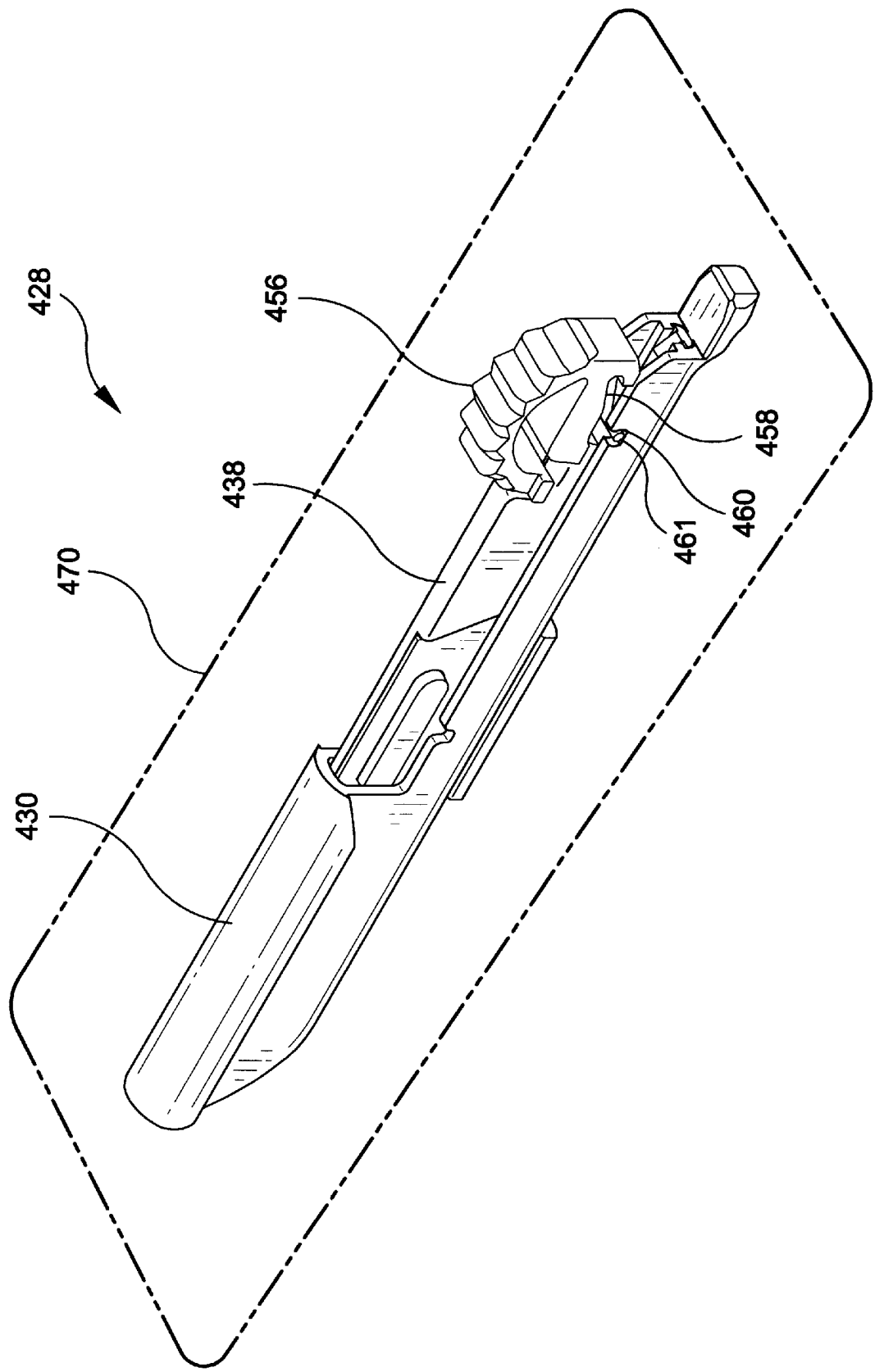
FIG. 24 is a perspective view of the cartridge of the scalpel of the invention.

Preferably, cartridge 428, with blade holder 438 in the proximal position where blade 446 is protected, is placed in a package 470, indicated in phantom in FIG. 24, formed from materials substantially resistant to the passage of microorganisms and package 470 is sealed. Preferably sealed package 470 is then exposed to conditions that would render any microorganisms inside the package substantially non-viable. Packaged cartridges then may be considered "sterile" until the package is opened to arm the reusable handle. Preferably, the handles are subjected to a cleaning and sterilization process by the practitioner prior to their presentation for the cartridge loading. Suitable materials for forming package 470 include, but are not limited to, paper, nonwoven materials such as spun-bonded polyolefin and the like, polymeric films, metallic foils and composites of these materials. Suitable techniques for rendering microorganisms within package 470 non-viable include, but are not limited to, exposure to chemical agents such as ethylene oxide, gaseous hydrogen peroxide and the like, ionizing radiation, such as gamma radiation from $Co^{60}$, electron beam radiation, dry heat and steam sterilization. When selecting materials for forming scalpel 410 and package 470, consideration of the particular materials' tolerance for the sterilization method should be made.

A method for preparing surgical scalpel 410 for use includes providing handle 412 with proximal end 414, a open distal end 416 and sidewalls 418 that define upwardly open cavity 420 with bottom 422 that has open void 424 therein. Sidewalls 418 each have elongate channel 426. The method of the invention preferably further includes providing sealed package 470 containing cartridge 428. The method then includes opening package 470 and exposing cartridge 428 and removing the cartridge from the package. The cartridge is then fitted into cavity 420, pressed into the handle thereby forming scalpel 410.

Referring now to FIGS. 34–42, a further embodiment of the scalpel 510 of the invention includes an elongate handle 512 having a proximal end 514, a open distal end 516 and sidewalls 518 that define an open cavity 520 therethrough, and wherein at least one of sidewalls 518, preferably both sidewalls 518, has an opening 522 therethrough. Scalpel 510 further includes a removable cartridge 524 that is mounted within cavity 520, that includes a shield 526. Shield 526 releasably retains cartridge 524 within the cavity 520. Cartridge 524 also has a blade holder 528 with a proximal end 530 and a distal end 532 mounted within shield 526 for slidable movement between a proximal, best seen in FIG. 37, and a distal position, best seen in FIG. 20. Blade holder 528 has a latch 534 for engaging shield 526 for releasably retaining blade holder 528 in the proximal position and for engaging handle 512 for releasably retaining blade holder 528 in the distal position. There is a blade 536 fixedly attached to blade holder 528 disposed so that when blade holder 528 is in the distal position, blade 536 projects distally from handle 512 and when blade holder 528 is in the proximal position blade 536 is within shield 526 and handle 512 thus substantially protected from inadvertent exposure.

Figure 34:
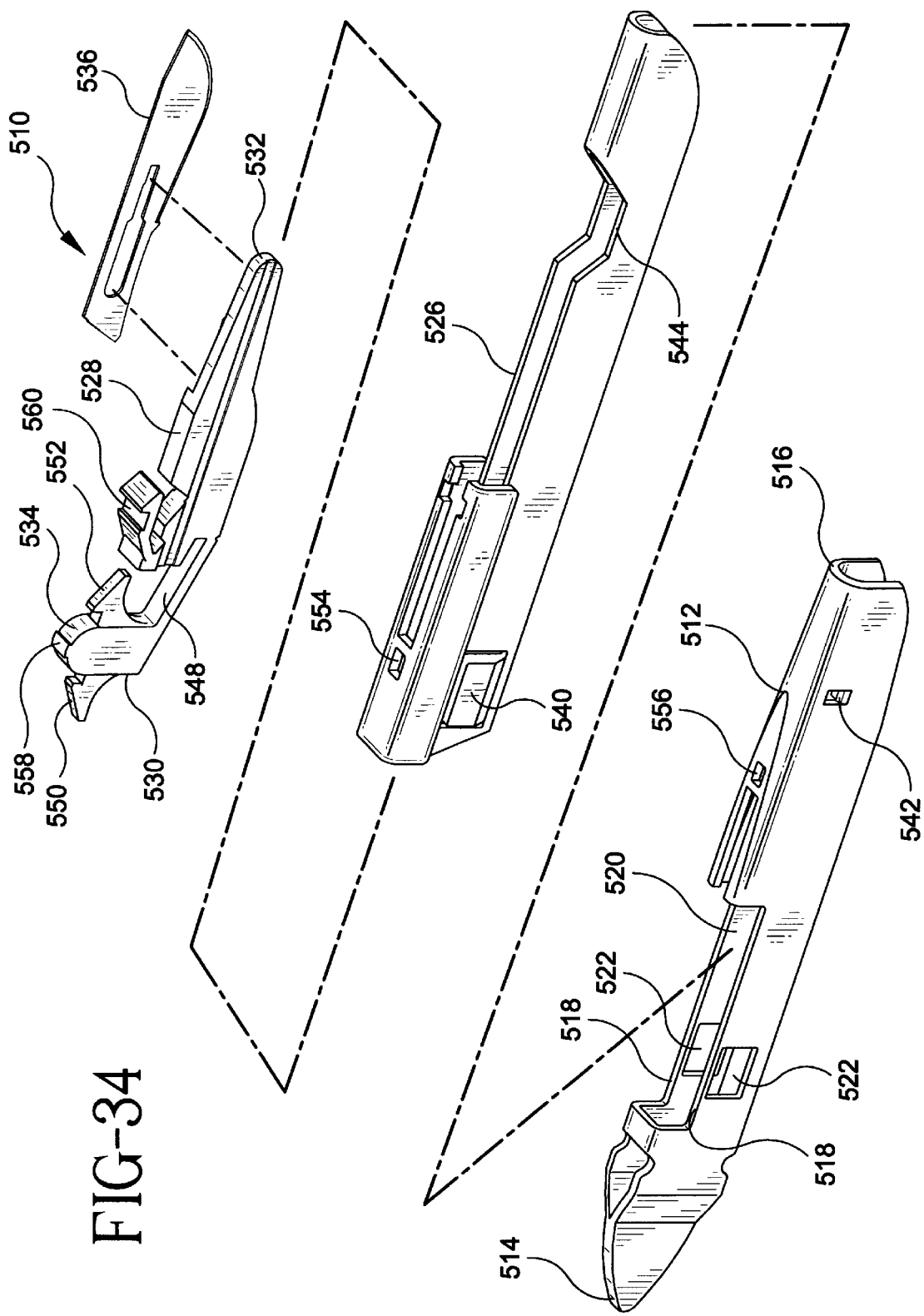
FIG. 34 is an exploded perspective view of a further embodiment of the scalpel of the invention.
Figure 36:
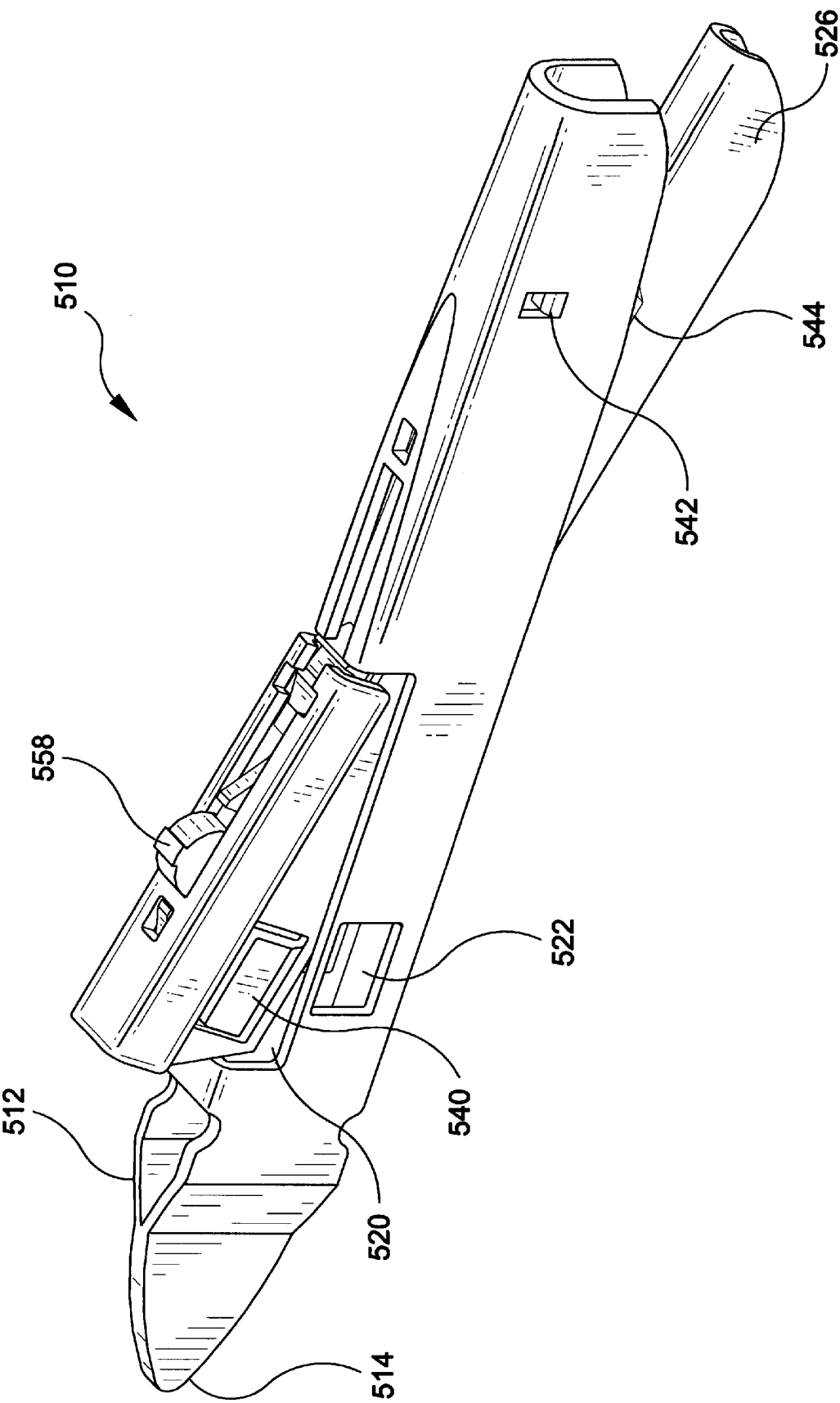
FIG. 36 is a perspective view of the scalpel of FIG. 34 partially assembled.
Figure 37:
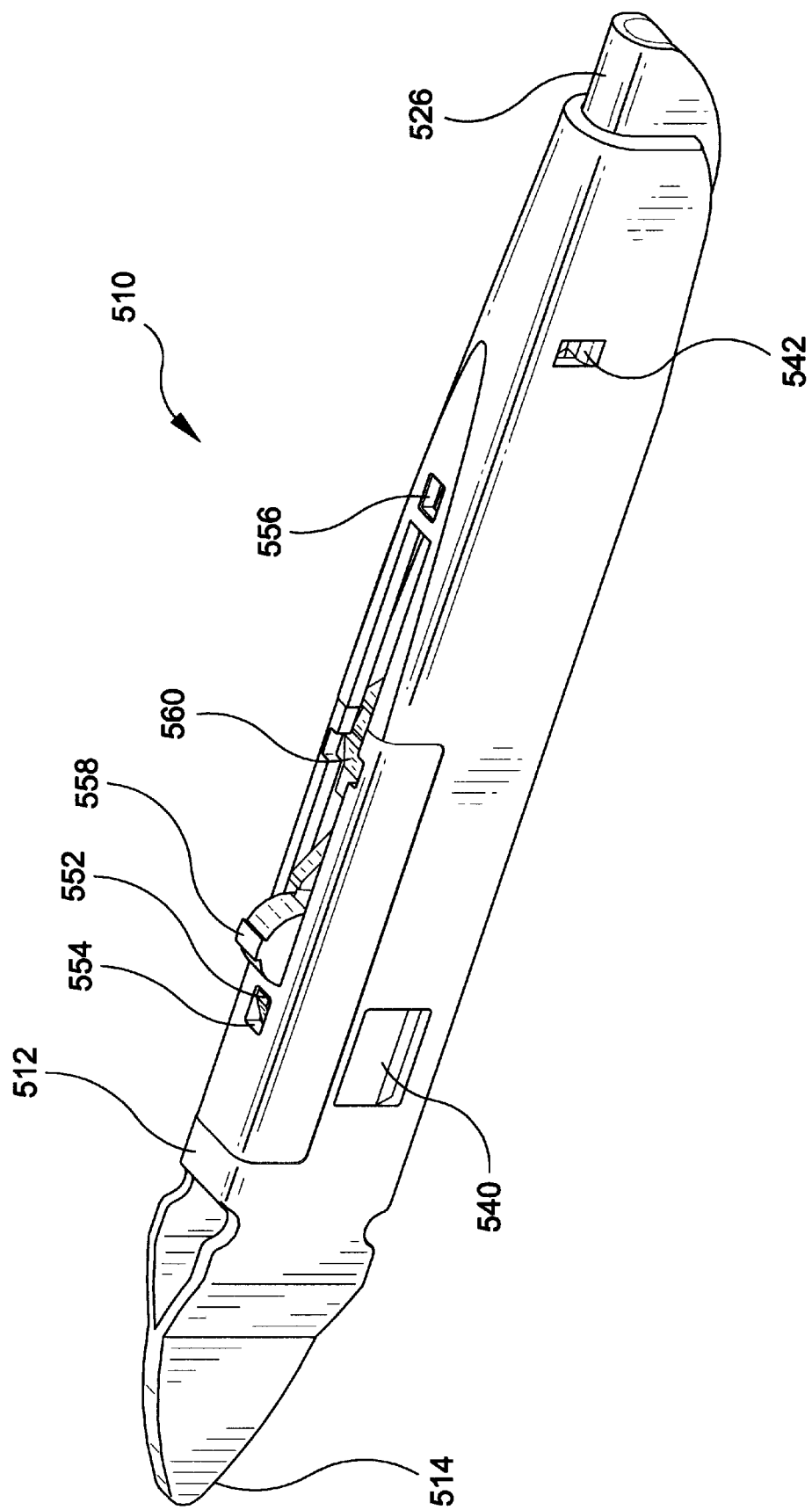
FIG. 37 is a perspective view of the scalpel of FIG. 34 fully assembled with the blade retracted.
Figure 38:
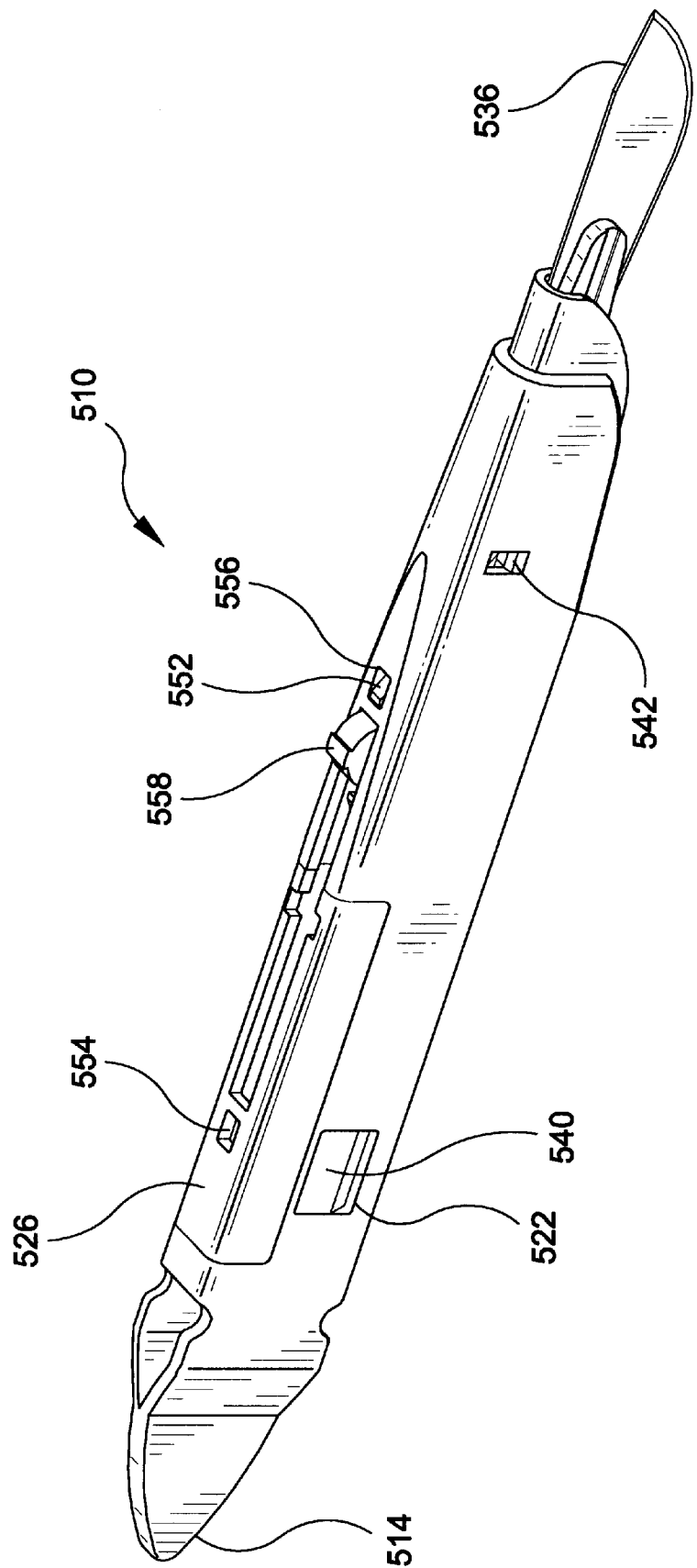
FIG. 38 is a perspective view of the scalpel of FIG. 34 with the blade extended.

As shown in FIGS. 34, 36 and 37, cartridge 524 is releasably retained in cavity 520 by a proximal protuberance 540, preferably two proximal protuberances 540, on shield 526 sized and shaped to engage each of the openings 522 in sidewalls 528 of handle 512 and an inward projection 542 on handle 512 sized and shaped to engage releasably an opening 544 in shield 526 when cartridge 524 is placed into cavity 520 to retain the cartridge in the cavity. Projection 542 disengages from opening 544 when blade holder 528 is retracted to the proximal position and a practitioner applies digit pressure to protuberances 540, thereby to release cartridge 524 from cavity 520 so that it may be removed from handle 512 for disposal.

Latch 534 releasably retains blade holder 528 in said proximal and said distal positions includes a cantilever portion 548 of the blade holder having a first lug 550 and a second lug 552 projecting outwardly therefrom. Cantilever 548 is sized and shaped so that first lug 550 is disposed to engage a first stop 554 in shield 526 when blade holder 528 is in proximal position, best seen in FIGS. 39 and 40, and second lug 552 is disposed to engage a second stop 556 in handle 512 when blade holder 528 is in the distal position, best seen in FIGS. 41 and 42 when cartridge 524 is placed in cavity 520. Cantilever 548 preferably includes a digit press surface 558 that projects upwardly above sidewalls 518 to allow the practitioner to deflect the cantilever to release lugs 550 and 552 and move blade holder 528 between the proximal and distal positions. Blade holder 528 also includes a deflectable wedge 560, best seen in FIGS. 25, 29 and 40, that is disposed to engage shield 526 when cartridge 524 is not mounted in handle 512, and to be deflected downwardly to disengage from shield 526 when cartridge 524 is mounted in handle 512. Wedge 560 substantially prevents movement of blade holder 528 with respect to shield 526 when cartridge 524 is not mounted in handle 512.

Figure 35:
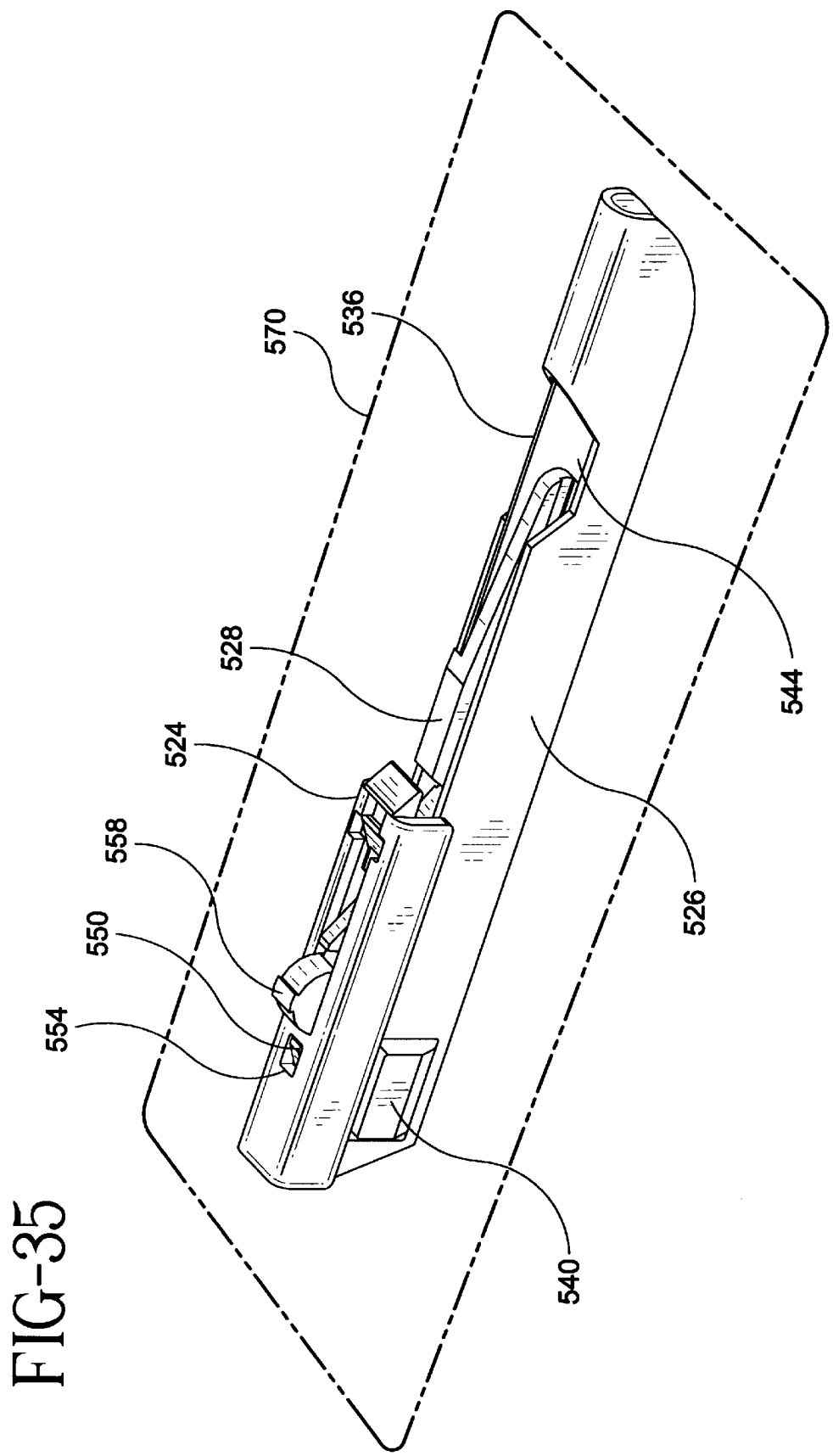
FIG. 35 is a perspective view of the cartridge of the invention of FIG. 34 in a package.

Preferably, cartridge 524, with blade holder 528 in the proximal position where blade 536 is protected, is placed in a package 570, indicated in phantom in FIG. 35, formed from materials substantially resistant to the passage of microorganisms and package 570 is sealed. Preferably sealed package 570 is then exposed to conditions that would render any microorganisms inside the package substantially non-viable. Packaged cartridges then may be considered "sterile" until the package is opened to arm the reusable handle. Preferably, the handles are subjected to a cleaning and sterilization process by the practitioner prior to their presentation for the cartridge loading. Suitable materials for forming package 570 include, but are not limited to, paper, nonwoven materials such as spun-bonded polyolefin and the like, polymeric films, metallic foils and composites of these materials. Suitable techniques for rendering microorganisms within package 570 non-viable include, but are not limited to, exposure to chemical agents such as ethylene oxide, gaseous hydrogen peroxide and the like, ionizing radiation, such as gamma radiation from $Co^{60}$, electron beam radiation, dry heat and steam sterilization. When selecting materials for forming scalpel 510 and package 570, consideration of the particular materials' tolerance for the sterilization method should be made.

The scalpel of the invention provides practitioners with a scalpel that has the "feel" and "heft" of traditional reusable scalpels while additionally providing both practitioners and support personnel with a shielded blade that is unlikely to be inadvertently exposed. The removable cartridge allows the use of a sterile sharp blade for the procedure and substantially allows the blade to be protected from inadvertent exposure both during preparation for the procedure and after the procedure.

What is claimed is:

1. A surgical scalpel comprising:

an elongate handle having a proximal end, a open distal end and sidewalls that define an upwardly open cavity with a bottom having an open void therein, said sidewalls each having an elongate channel therein;

a cartridge removably mounted within said cavity, said cartridge including a shield and having releasable retention means for retaining said cartridge within said cavity;

a blade holder with a proximal end and a distal end mounted within said shield for slidable movement between a proximal and a distal position, said blade holder having latch means for engaging said handle and said shield to retain releasably said blade holder in said distal position and said proximal position; and a blade fixedly attached to said blade holder so that when said blade holder is in said distal position, said blade projects distally from said handle and when said blade holder is in said proximal position said blade is within said shield and said handle and substantially protected from inadvertent exposure.

2. The scalpel of claim 1 wherein said releasable retention means for retaining said cartridge in said cavity include a proximal protuberance on said shield sized and shaped to engage a void in said sidewall of said handle and a keeper on said shield sized and shaped to engage releasably said opening in said bottom of said cavity, when said cartridge is placed into said cavity to retain said cartridge in said cavity and to disengage from said opening when said blade holder is retracted and a practitioner applies digit pressure to said keeper, thereby to release said cartridge from said cavity.

3. The scalpel of claim 1 wherein latch means for engaging said handle and releasably retaining said blade holder in said proximal and said distal positions comprises a cantilever portion of said blade holder having two lugs projecting outwardly therefrom, said cantilever being sized and positioned to engage said channels in said sidewalls when said cartridge is placed in said cavity, and wherein said channels each include a proximal stop position and a distal stop position for releasably retaining said lugs when said blade holder is in said proximal position and said distal position.

4. The scalpel of claim 3 wherein said cantilever further comprises a digit press surface that projects above said sidewalls when said cartridge is placed in said cavity in said handle.

5. The scalpel of claim 3 wherein said cantilever further comprises a tab with a projection sized and positioned to engage said shield and substantially to prevent movement of said blade holder from said proximal position to said distal position with respect to said shield unless said cartridge is mounted in said cavity in said handle, said tab being disengaged from said shield when said cartridge is mounted in said cavity in said handle thereby allowing movement of said blade holder with respect to said shield and said handle.

6. The surgical scalpel of claim 1 wherein said blade holder further comprises an outward projection and said blade further comprises an aperture therethrough sized to engage said outward projection, said blade being fixedly attached to said blade holder by positioning said aperture in said blade over said projection.

7. The surgical scalpel of claim 6 wherein said blade is fixedly attached to said outward projection of said blade holder by bonding technique selected from the group consisting of heat staking and adhesive bonding.

8. The surgical scalpel of claim 1 wherein said blade holder is formed from a thermoplastic material selected from the group consisting of polypropylene, polyethylene, polycarbonate, polysulfone, polyacetal and polyamide.

9. The surgical scalpel of claim 1 wherein said shield is formed from a thermoplastic material selected from the group consisting of polypropylene, polyethylene, polysulfone, polycarbonate, polyacetal, and polyamide.

10. The surgical scalpel of claim 9 wherein said shield is formed from a substantially transparent material.

11. The surgical scalpel of claim 1 wherein said handle is formed from a material selected from the group consisting of machined metal, formed powdered metal and thermoplastic materials.

12. The surgical scalpel of claim 1 further comprising said cartridge being placed in a package formed from materials substantially resistant to the passage of microorganisms and exposed to conditions that render any microorganisms therein substantially nonviable.

13. A cartridge removably mountable within a cavity in a handle to form a surgical scalpel comprising:
    a shield;
    a blade holder with a proximal end and a distal end mounted within said shield for slidable movement between a proximal and a distal position, said blade holder having latch means for engaging a handle and said shield to retain releasably said blade holder in said distal position and said proximal position; and
    a blade fixedly attached to said blade holder so that when said blade holder is in said distal position with respect to said shield and said cartridge is mounted in the handle, said blade projects distally and when said blade holder is in proximal position with respect to said shield said blade is within said shield and substantially protected from inadvertent exposure.

14. The cartridge of claim 13 wherein said blade holder is substantially retained in said proximal position with respect to said cartridge wherein said blade is substantially protected from inadvertent exposure when said cartridge is not mounted in a handle.

15. The cartridge of claim 13 further comprising said cartridge being placed in a package formed from materials substantially resistant to the passage of microorganisms and exposed to conditions that render any microorganisms therein substantially nonviable.

16. A surgical scalpel comprising:
    an elongate handle having a proximal end, a open distal end and sidewalls that define an upwardly open cavity with a bottom having an open void therein, said sidewalls each having an elongate channel therein;
    a cartridge removably mounted within said cavity, said cartridge including a shield and having a distal protuberance on said shield sized and shaped to engage a void in said sidewall of said handle and a keeper sized and shaped to engage releasably said opening in said bottom of said cavity, when said cartridge is placed into said cavity, for retaining said cartridge within said cavity, said keeper being disengaged from said opening when said blade holder is retracted and a practitioner applies digit pressure to said keeper, thereby to release said cartridge from said cavity;
    a blade holder with a proximal end and a distal end mounted within said shield for slidable movement with respect to said shield and said handle between a proximal and a distal position, said blade holder having latch means for engaging said handle and said shield to retain releasably said blade holder in said distal position and said proximal position; and
    a blade fixedly attached to said blade holder so that when said blade holder is in said distal position, said blade projects distally from said handle and when said blade holder is in said proximal position said blade is within said shield and said handle and substantially protected from inadvertent exposure.

17. A method for preparing a surgical scalpel for use comprises:
    providing a handle for a scalpel having a proximal end, a open distal end and sidewalls that define an upwardly open cavity with a bottom having an open void therein, said sidewalls each having an elongate channel therein;
    providing a sealed package containing a cartridge removably mountable within said cavity in said handle comprising a blade holder with a proximal end and a distal end, said blade holder having means for removably mounting said cartridge to the handle, a blade fixedly attached to said blade holder so that said blade projects distally when said cartridge is mounted to the handle and a shield mounted on said blade holder for slidable movement between a proximal position wherein said shield substantially prevents inadvertent access to said blade and a distal position wherein said shield is substantially contained within the handle and said blade is exposed for use, said shield having latch means for engaging said blade holder and releasably retaining said blade holder in said distal position and said proximal position;
    opening said package and exposing said cartridge;
    removing said cartridge from said package;
    fitting said proximal end of said cartridge into said cavity in said handle and pressing said cartridge into said handle thereby forming a scalpel; and
    moving said blade holder from said proximal position to said distal position, thereby exposing said blade for use.

18. A surgical scalpel comprising:
    an elongate handle having a proximal end, a open distal end and sidewalls that define an open cavity therethrough, and wherein at least one of said sidewalls having a void therethrough;
    a cartridge removably mounted within said cavity, said cartridge including a shield, said shield having releasable retention means for retaining said cartridge within said cavity;

a blade holder with a proximal end and a distal end mounted within said shield for slidable movement between a proximal and a distal position, said blade holder having latch means releasably retaining said blade holder in said distal position and said proximal position; and a blade fixedly attached to said blade holder so that when said blade holder is in said distal position, said blade projects distally from said handle and when said blade holder is in said proximal position said blade is within said shield and said handle and substantially protected from inadvertent exposure.

19. The scalpel of claim 8 wherein said releasable retention means for retaining said cartridge in said cavity include a proximal protuberance on said shield sized and shaped to engage said void in said sidewall of said handle and an inward projection on said handle sized and shaped to engage releasably an opening in said shield when said cartridge is placed into said cavity to retain said cartridge in said cavity and to disengage from said opening when said blade holder is retracted and a practitioner applies digit pressure to said protuberance, thereby to release said cartridge from said cavity.

20. The scalpel of claim 18 wherein latch means for engaging said shield to retain said blade holder in said proximal position and releasably engaging said handle for releasably retaining said blade holder in said distal position comprises a cantilever portion of said blade holder having a first lug and a second lug projecting outwardly therefrom, said cantilever being sized and shaped so that said first lug is disposed to engage a first stop in said shield when said blade holder is in said proximal position and said second lug is disposed to engage a second stop in said handle when said cartridge is placed in said cavity.

21. The scalpel of claim 20 wherein said cantilever further comprises a digit press surface that projects above said sidewalls when said cartridge is placed in said cavity in said handle for applying digit pressure and to deflect said cantilever to release said lugs from said stops and facilitate said movement between said proximal and said distal positions.

* * * * *